US008283452B2

(12) United States Patent
Kapteyn et al.

(10) Patent No.: US 8,283,452 B2
(45) Date of Patent: *Oct. 9, 2012

(54) ASSAY FOR THE SEPARATION AND QUANTIFICATION OF HEMAGGLUTININ ANTIGENS

(75) Inventors: Johan C. Kapteyn, Wageningen (NL); Fija M. Lagerwerf, Leiderdorp (NL)

(73) Assignee: Crucell Holland B.V., Leiden (NL)

( * ) Notice: Subject to any disclaimer, the term of this patent is extended or adjusted under 35 U.S.C. 154(b) by 217 days.

This patent is subject to a terminal disclaimer.

(21) Appl. No.: 12/587,136

(22) Filed: Oct. 2, 2009

(65) Prior Publication Data

US 2010/0041022 A1    Feb. 18, 2010

Related U.S. Application Data

(63) Continuation of application No. 10/592,743, filed on Sep. 13, 2006, now Pat. No. 7,638,608.

(30) Foreign Application Priority Data

Mar. 17, 2004  (WO) ................ PCT/EP2004/050318
Mar. 3, 2005   (WO) ................ PCT/EP2005/050957

(51) Int. Cl.
    *A23J 1/00*    (2006.01)
    *A61K 39/205*  (2006.01)
(52) U.S. Cl. ................. 530/412; 424/184.1; 424/210.1; 530/396
(58) Field of Classification Search ........................ None
See application file for complete search history.

(56) References Cited

U.S. PATENT DOCUMENTS

| 7,304,031 B2 | 12/2007 | Opstelten et al. | |
|---|---|---|---|
| 7,638,608 B2 * | 12/2009 | Kapteyn et al. | ............... 530/412 |
| 7,687,611 B2 * | 3/2010 | Kapteyn et al. | ............... 530/412 |
| 2006/0051742 A1 | 3/2006 | Kapteyn et al. | |
| 2006/0186049 A1 | 8/2006 | Boyes et al. | |

FOREIGN PATENT DOCUMENTS

WO    WO 2005/090390    9/2005

OTHER PUBLICATIONS

Basak and Compans, Improved Separation of Glycosylated Tryptic Peptides by RP-HPLC, 1981, Journal of High Resolution Chromatography and Chromatography Communications, vol. 4, pp. 302-304.*
Bizhanov et al., Influence of Detergents of Measurement of Influenza A Virus Haemagglutinin Content in Inactivated Influenza Vaccine by Single Radial Immunodiffusion, Acta Virol., 1988, pp. 252-260, vol. 32.
Calam et al., Isolation of Influenza Viral Proteins by Size-Exclusion and Ion-Exchange High-Performance Liquid Chromatography: The Influence of Conditions on Separation, Journal of Chromatography, 1984, pp. 285-292, vol. 296.

Chen et al., Temperature programming and gradient elution in reversed-phase chromatography with packed capillary columns, 1997, Journal of Chromatography, vol. 788, pp. 51-61.
Chen et al., Temperature selectivity effects in reversed-phase liquid chromatography due to conformation differences between helical and non-helical peptides, J. Chromatogr A. Aug. 22, 2003 pp. 45-61, vol. 1010, No. 1.
Deshpande et al., Glycosylation affects cleavage of an H5N2 influenza virus hemagglutinin and regulates virulence, PNAS. 1987, pp. 36-40, vol. 84.
Dolan et al., Temperature selectivity in reversed-phase high performance liquid chromatography, Journal of Chromatography, 2002, pp. 195-205, vol. 965.
Galvani et al., Protein alkylation in the presence/absence of thiourea in proteome analysis: A matrix assisted laser desorption/ionization-time of flight-mass spectrometry investigation, 2001, Electrophoresis, vol. 22, pp. 2066-2074.
Glocker et al., Disulfide linkages in the in vitro refolded intermediates of recombinant human macrophage-colony-stimulating factor: analysis of the sulfhydryl alkylation of free cysteine residues by fast-atom bombardment mass spectrometry, Proc Natl Acad Sci, USA, Jun. 21, 1994, pp. 5868-5872, vol. 91. No. 13.
International Association of Biological Standardization, Symposia Series in Immunobiological Standardization, 1973, pp. 378-381, vol. 20.
Johannsen et al., Quantification of haemagglutinin of influenza Tween-ether split vaccines by immunodiffusion, Vaccine, Supplement 1985, pp. 235-240, vol. 3.
Kemp et al., Separation of Influenza Hemagglutinin Tryptic Glyco Peptides by Ion Pair Reverse Phase High Performance Liquid Chromatography, Journal of Biochemical and Biophysical Methods. 1980, pp. 61-63, vol. 3, No. 1.
Nostelbacher et al., Separation and quantitation of metallothionein isoforms from liver of untreated rats by ion-exchange high-performance liquid chromatography and atomic absorption spectrometry, J. Chromatogr. B. Biomed Sci. App., Jul. 21, 2000, pp. 273-282, vol. 744, No. 2.
Office Action for U.S. Appl. No. 11/119,631, dated Aug. 12, 2008.
Office Action for U.S. Appl. No. 11/119,631, dated Feb. 5, 2009.
Office Action for Application No. 11/119,631, dated Oct. 9. 2007.
PCT International Search Report, PCT/EP2005/050957 dated May 24, 2005.
Phelan et al., Gradient Optimization Principles in Reversed-Phase High-Performance Liquid Chromatography and the Separation of Influenza Virus Components, Journal of Chromatography, 1983, pp. 55-66, vol. 266.
Puehler et al., An Interferon-γ-binding Protein of Novel Structure Encoded by the Fowlpox Virus, 2003, vol. 278, No. 9, pp. 6905-6911.
Skehel et al., Studies on the Primary structure of the influenza virus hemagglutinin, PNAS, 1975, pp. 93-97, vol. 72.

(Continued)

*Primary Examiner* — Benjamin P Blumel
(74) *Attorney, Agent, or Firm* — TraskBritt

(57) ABSTRACT

Described are methods for separating hemagglutinin (HA) antigens, comprising the steps of applying a reduced and derivatized antigen preparation comprising solubilized HA antigens and a detergent in a pH controlled solution, on a Reversed-Phase High-Performance Liquid Chromatography (RP-HPLC) column; and eluting the HA antigens from the column with an ion pairing agent in an organic mobile phase. The invention further relates to quantifying methods using the methods for separating the antigens with the further step of measuring the peak area of the eluted antigen in a chromatogram resulting from the elution step.

20 Claims, 24 Drawing Sheets

OTHER PUBLICATIONS

Van Der Zee et al., Purification of Detergent-Extracted Sendai Virus Proteins by Reversed-Phase High-Performance Liquid Chromatography, 1983, pp. 577-584, vol. 266.

Vellekamp et al., Empty capsids in column-purified recombinant adenovirus preparations, Hum Gene Ther. Oct. 10, 2001 pp. 1923-1936, vol. 12, No. 15.

Walcher et al., Operational variables in high-performance liquid chromatography-electrospray ionization mass spectrometry of peptides and proteins using poly(styrene-divinylbenzene) monoliths, J. Chromatogr. A. Oct 22, 2004; pp. 107-117, vol. 1053, No. 1-2.

Willkommen et al., The influence of pH and Ionic Strength of the Single Radial Immunodiffusion Test in Qualitative Assay of Influenza Virus Haemagglutinin, Acta Virol., 1983, pp. 407-411, vol. 27.

Wood et al., An improved single-radial-immunodiffusion technique for the assay of influenza haemagglutinin antigen: application for potency determinations of inactivated whole virus and subunit vaccines, Journal of Biological Standardization, 1977, pp. 237-247, vol. 5.

Office Action for U.S. Appl. No. 11/119,631, dated Aug. 24, 2009.

U.S. Appl. No. 10/592,743, filed Sep. 13, 2006, Kapteyn et al., Novel Assay for the Separation and Quantification of Hemagglutinin Antigens.

U.S. Appl. No. 11/119,631, filed May 2, 2005, Kapteyn et al., Novel Assay for the Separation and Quantification of Hemagglutinin Antigens.

U.S. Appl. No. 11/657,202, filed Jan. 24, 2007, Opstelten et al., Methods and Means for Producing Proteins With Predetermined Post-Translational Modifications.

U.S. Appl. No. 11/888,776, filed Aug. 1, 2007, Opstelten et al., Methods and Means for Producing Proteins with Predetermined Post-Translational Modifications.

* cited by examiner

FIG. 8

Panel A

Panel B

US 8,283,452 B2

ASSAY FOR THE SEPARATION AND QUANTIFICATION OF HEMAGGLUTININ ANTIGENS

CROSS-REFERENCE TO RELATED APPLICATION

This application is a continuation of U.S. patent application Ser. No. 10/592,743, filed Sep. 13, 2006, now U.S. Pat. No. 7,638,608, which is a national stage entry of PCT International Patent Application No. PCT/EP2005/050957, filed on Mar. 3, 2005, designating the United States of America, and published, in English, as PCT International Publication No. WO 2005/090390 A1 on Sep. 29, 2005, which applications claim priority to PCT International Patent Application No. PCT/EP2004/050318, filed Mar. 17, 2004, the contents of the entirety of each of which are incorporated by this reference.

FIELD OF THE INVENTION

The invention relates to the field of vaccine manufacturing. More in particular, the invention relates to the production of influenza vaccines and the determination of antigen concentration in influenza virus preparations.

BACKGROUND OF THE INVENTION

Influenza viruses are generally divided into three types: A, B, and C, based on the antigenic differences between their nucleoprotein and matrix protein antigens. Influenza A viruses are further divided into subtypes depending on the antigenic nature of the two major viral surface proteins, the hemagglutinin (HA) and neuraminidase (NA) proteins. Currently, 15 subtypes of HA are known (Lamb and Krug, 2001). Both HA and NA carry antigenic epitopes. Antibodies that are raised against HA and NA are associated with resistance to infection and/or illness in humans and animals. The efficacy of a vaccination against influenza is largely determined by the amount of immunogenic HA in a vaccine (Wright and Webster, 2001).

For several decades the HA content of influenza whole-virus and split vaccines derived from this, has been assayed using Single Radial Immunodiffusion (SRID). In this assay, influenza virions are disrupted by detergent and submitted to immunodiffusion for three days at room temperature in antibody-loaded agarose gels. Upon gel staining, the precipitation zone diameters of antigen-antibody complexes are measured, and the antigen content of virus preparations of a certain subtype is calculated by using a calibration curve obtained with a whole virus reference batch of this subtype (NIBSC, Hertfordshire, UK) with a known HA content (Wood et al., 1977).

However, this SRID assay has a number of disadvantages. Apart from being time consuming, laborious and not leaving room for very high throughput (Wood et al., 1977), the quantification of HA by SRID was shown to be inaccurate when analyzing split vaccines or subunit vaccines (Johannsen et al., 1985). In addition, the virus sample environmental background (its pH and ionic strength) and the choice of detergent for disintegrating the influenza virus and its HA were shown to affect the determination of the HA titer (Willkommen et al., 1983; Bizhanov et al., 1988). Despite all shortcomings of the SRID assay, and calls from experts in the field that in addition to the SRID assay a physico-chemical quantification method should be used for the quantification of HA (Pereira, 1973; Johannsen et al., 1985), immunodiffusion techniques are still the only methods approved by the regulatory authorities for the evaluation of influenza vaccines.

A Reversed-Phase High Performance Liquid Chromatography (RP-HPLC) method to separate influenza virus components has been described (Phelan and Cohen, 1983). Viral proteins were solubilized and denatured in guanidine-HCl, and reduced by incubation with dithiotreitol (DTT) for several hours at room temperature. It is a well-recognized fact in the art that, under denaturing conditions upon reduction, mature and activated HA0 falls apart in the relatively hydrophilic subunit HA1 and the hydrophobic subunit HA2, the latter still containing the trans membrane domain of the original HA0. Subsequently, analysis was performed by RP-HPLC at room temperature on an (C8) Aquapore column, applying a linear gradient of 0.05% TFA in water to 0.05% TFA in acetonitrile. However, the separation of the various virus components was far from optimal, whereas the recovery was low and not quantitative, presumably due to aggregation of the virus components and/or nonspecific adsorption to the HPLC system/column. In addition, in this HPLC assay HA2 could not be detected, presumably because it had been trapped on the column matrix due to its strong hydrophobic nature.

Kemp et al. (1980) also discloses a method for separating influenza HA using RP-HPLC: radiolabeled tryptic glycopeptides (small parts) of HA are pre-isolated from SDS/PAGE gels and subsequently analyzed by HPLC. The method disclosed by Kemp et al. has the disadvantage of not being suitable for a high-throughput system, because the isolation from gel renders the method rather laborious. Moreover, the chromatographs clearly indicate the poor resolution of the peaks, overlapping with numerous other viral peaks, which makes that the method cannot be used for quantitative purposes. The isolation of numerous bands related to different peptides of different size from gel makes that the method is not suitable for very accurate quantification and repeatability. Moreover, the method of Kemp et al. is not suitable for real-life (non-radiolabeled) samples as the radiolabel is detected, and not suitable for crude sample analyses.

In yet another study (Van der Zee et al., 1983), a method has been disclosed for the purification of Sendai virus envelope proteins using RP-HPLC. Although Van der Zee et al. state that some proteins could be recovered in pure form, this was only assessed by SDS/PAGE, which method is not a very accurate means to show purity of a sample. The chromatograms show that resolution is poor: this indicates that any accurate quantification, based on the HPLC chromatograms is not possible using the purification method disclosed. Moreover, it seems that the detergent interferes with the peak of interest. Furthermore, carry-over of proteins from one analysis to the other is significant. In general, it is clear that the art does not disclose methods and means for an accurate determination of HA concentration in either crude or purified HA samples.

Clearly, there is a strong need for a robust, accurate and fast method for reliable separation and quantification of HA in upstream- and downstream-process preparations, as well as for final vaccine formulations.

SUMMARY OF THE INVENTION

The invention relates to methods for separating hemagglutinin ("HA") antigens, comprising the steps of applying a reduced and derivatized antigen preparation comprising solubilized HA antigens and a detergent in a pH controlled solution, on a Reversed Phase High Performance Liquid Chromatography (RP-HPLC) column; and eluting the HA antigens from the column with an ion-pairing agent in an organic mobile phase. Certain embodiments of the invention relate to methods wherein elution is performed at a temperature between about 25° C. and about 70° C., preferably between about 40° C. and about 70° C., more preferably between about 50° C. and about 70° C., and, most preferably, between about 60° C. and 70° C. In certain embodiments, the method comprises a step wherein the antigens are cleaved by a protease, such as trypsin.

Also described are methods for quantifying the HA titer of an HA antigen preparation, such methods comprising the method of separating hemagglutinin (HA) antigens as described herein, with the further step of measuring the peak area of the eluted antigen in a chromatogram resulting from the elution step.

DESCRIPTION OF THE FIGURES

FIG. 8. SDS-PAGE silver staining of the RP-HPLC fractions 1, 2b, 2a, 3, 4, 5a, 5b and 5c of FIG. 7. 0.19 ug HA of the Duck/Sing strain was used as a positive control.

DETAILED DESCRIPTION

Figure 1:
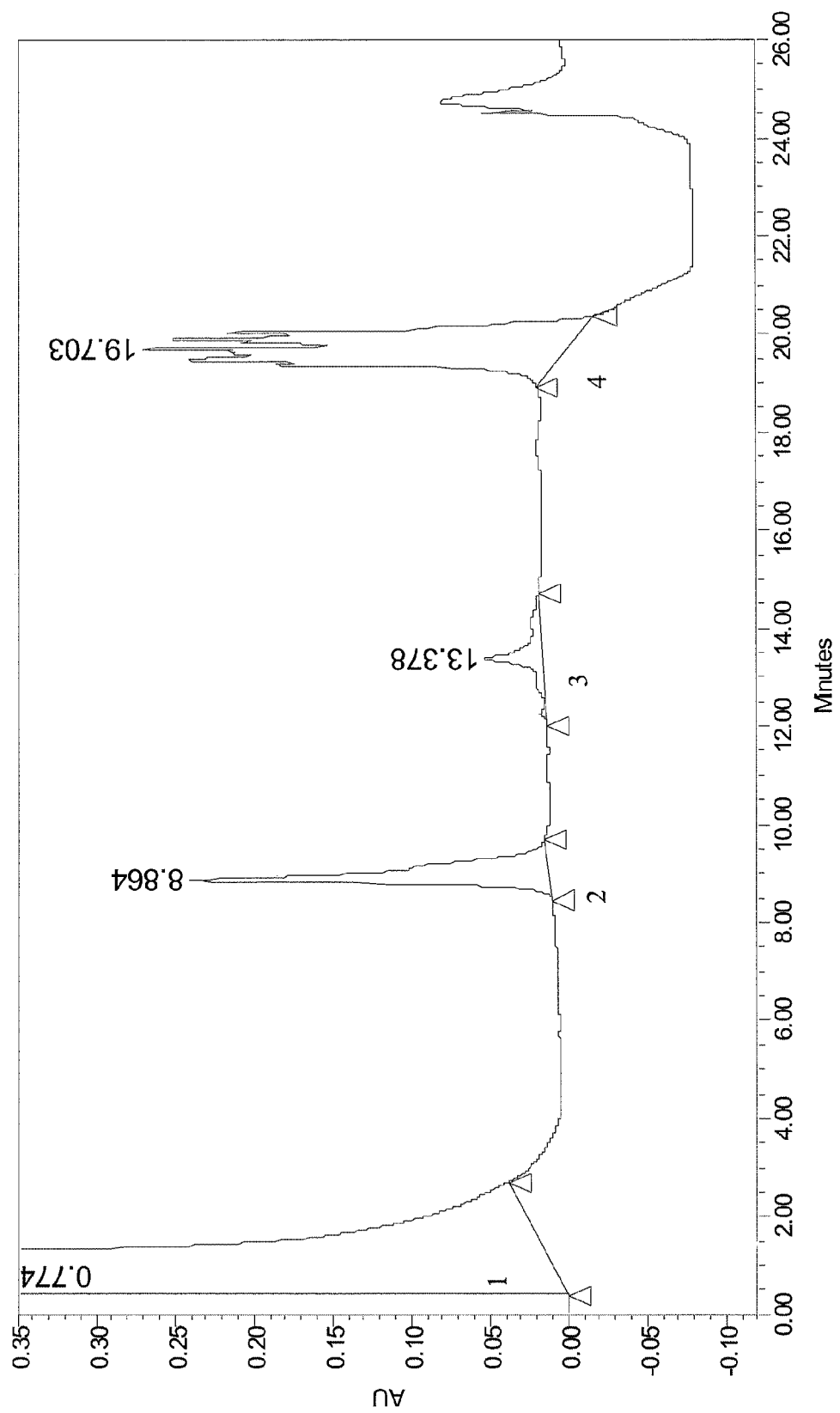
FIG. 1. Reversed-Phase HPLC of egg-derived, reduced and alkylated influenza A/Panama/2007/99 (Resvir-17; H3N2) 02/100. An amount corresponding to 10.0 µg HA (as determined by SRID) was injected. Numbers 1-4 correspond to the fractions applied on SDS-PAGE of FIG. 2.

Here, a novel separation and quantification assay for the determination of hemagglutinin (HA) concentration by Reversed-Phase High-Performance Liquid Chromatography (RP-HPLC) is disclosed. The problem with the RP-HPLC methods that have been described in the art for separation of the antigens from influenza virus was that the separation was not optimal, with poor resolution of the protein peaks of interest, and that the recovery was low and not quantitative. The inventors of the invention have now solved many of these problems by using a certain RP-HPLC assay in a set-up in which the antigen is reduced in the presence of a detergent, after which an inert derivatization of the antigen preparation is performed thereby protecting the sulfhydryl groups on the antigen. Preferably, for this step, an alkylating agent is added to render a reduced and alkylated antigen preparation and wherein the antigen is present in a pH controlled solution. It was found that by increasing the temperature during elution of the antigens from the RP-HPLC column, the recovery and the reproducibility of the assay was increased. The assays known from the art were performed at room temperature.

The inventors herein have also found that it is preferred to select a column material that is suitable to be used at higher temperatures of up to about 70° C. Preferred column material is therefore polymer-based, which generally can be used in these high temperature ranges. It is also preferred to keep the solution in which the antigen is dissolved pH controlled, preferably at neutral pH values. Preferably, values between about 5 and about 9 are used, more preferably values between about 6 and about 8 are used, while it is most preferred to use pH values between about 7 and about 8. Methods for buffering solutions are well known in the art and are herein not further elaborated on.

The virus preparation can be brought on the column, eluted from the column and the quantities of the antigens can be calculated from the specific peak areas all in a single day. It is thus a fast and robust method. Moreover, the methods clearly show that the process is accurate (as found in comparison to the SRID assay) and reproducible. The invention relates thus to a fast and accurate means for determining the HA concentration in different kinds of samples within the manufacturing process of influenza vaccines, thereby overcoming most of the problems associated with the methods known in the art.

In the disclosed assay, the quantification of HA is based on the peak area of HA1, which is well separated from the other vaccine components. The applicability of the invention is demonstrated for different influenza A subtypes, including H1N1, H3N2, H5N3, and H7N7, strongly suggesting that the assay can be broadly applied for different hemagglutinin antigens. The Neuraminidase (NA) component of the strains is not limiting the broad applicability of the invention, as it relates to the separation of the HA component. It is assumed that the invention will also be applicable for influenza B subtypes, as well as for other viruses comprising hemagglutinin antigens that behave in a similar manner on HPLC columns.

The invention relates to a novel method for separating hemagglutinin (HA) antigens, the method comprising the steps of applying a reduced and derivatized antigen preparation comprising solubilized HA antigens and a detergent in a pH controlled solution, on a Reversed-Phase High-Performance Liquid Chromatography (RP-HPLC) column; and eluting the HA antigens from the column with an ion pairing agent in an organic mobile phase.

In certain embodiments, influenza virus particles obtained from an upstream process of either egg-derived material or virus material from cell culture are first solubilized by the addition of a detergent, preferably a zwitterionic agent, more preferably ZWITTERGENT™, to a concentration of for example about 1% (w/v), but this is not critical to the invention. Subsequently, samples are treated with a protease such as trypsin (typically present on beads) to cleave all HA molecules into the subunits HA1 and HA2, which are only kept together by a single disulfide bridge upon this treatment.

As trypsin is hindered by the presence of high concentrations of SDS, SDS is preferably not used when the trypsin step is added to the method. If SDS is used, the concentration should be low enough not to inhibit the protease. Thus, it is preferred to use a detergent that does not inhibit the activity of the (possible) additional protease.

The disulfide bridge is then broken by addition of a reducing agent, preferably dithiotreitol (DTT) to a concentration of for example 25 mM, although other concentrations may also be used, and reduction takes place for about 10 minutes at about 90° C. As in some cases the samples acidify to pH values of 4.0 and become slightly milky and turbid, it is preferred to perform the reduction under buffered (relatively neutral pH) conditions, such as in 150 mM Tris-HCl, pH 8.0. To prevent re-association and/or complex formation of HA1 with HA2 and other proteins, it is highly preferred to have the sulfhydryl groups of all proteins protected, for instance by the addition of an alkylating agent, such as iodacetamide (IAA) or iodoacetic acid. Any inert derivatization of the —SH groups may be applied, such that no active groups remain. For example, any suitable sulfhydryl alkylating agent known in the art may be used. Examples of other suitable alkylating agents are N-ethylmaleimide; dithiobis(2-nitro)benzoic acid; nitrogen mustards, such as chlorambucil and cyclophosphamide; cisplatin; nitrosoureas, such as carmustine, lomustine and semustine; alkylsulfonates, such as busulfan; ethyleneimines, such as thiotepa; and triazines, such as dacarbazine. The person skilled in the art is aware of what compounds may be used to have the sulfhydryl groups protected and what compounds may be used to derivatize the antigen preparation, such that no active groups remain.

As disclosed herein, alkylation with IAA is usually performed at 37° C. in the dark for about 45 minutes, but other conditions (T, time) will work as well. This step is then preferably followed by the step of adding an alkylation-inhibiting agent, for instance through re-addition of DTT to neutralize all remaining IAA molecules, upon which the samples are ready for RP-HPLC analysis. The HPLC analysis may be performed by using a POROS R1/10 column (Applied Biosystems), but other comparable columns would work as well. Usually, an acetonitrile gradient from 20 to 35% is applied at a column temperature that may be as high as 70° C., but preferably around 65° C., as the column cannot withstand temperatures that are much higher. In this high temperature range, the HA1 peak is generally highest for this column. When the column material allows higher temperatures, the elution temperature may also be increased.

The column of choice is usually selected for its performance at high temperatures. Although silica-based columns such as C4 or C8 can be used, polymer-based columns, such as the POROS R1/10 column, are preferred as they can still perform well at temperatures as high as 70° C. As outlined herein, higher temperatures ensure a better recovery from the column, and thus in a better quantitative method.

In the course of the experiments, it was found that prolonged storage of the reduced/alkylated samples at 4° C. may result in a deformation of the HA1 peak in the RP-HPLC graphs, which would influence the accuracy of peak measurements and thus on the accuracy of the method. Although it does not count for crude samples, present in medium, this would limit the storage/shipment possibilities of the treated (reduced/alkylated) samples and thus on the overall usefulness of the method. This problem of deformation of the peak was solved by adding the reducing agent (exemplified by DTT) also after the alkylation step, thereby decreasing the harmful effects of the alkylating agent. So, the additional step of adding a reducing agent after alkylation, is highly preferred.

It was also found that certain concentrations of DTT increased the peak area of HA1 when the samples were analyzed immediately. In general, it is preferred to use concentrations of the reducing agent that are higher than about 4.4 mM, more preferably at least about 11 mM, and most preferably about 22 to about 25 mM.

Generally, when the method of the invention is carried out as a routine, using the same column for different runs, carry-over from HA from one run to another occurs (see, for an example, Van der Zee et al., 1983). To reduce the effect of carry-over, a wash step of the column with a detergent, such as 1% SDS or 1% ZWITTERGENT™ is highly recommended between different runs on the same column, to remove all residual HA from the column material.

Hemagglutinin (HA) antigens are well known in the art. Although the methods described herein have been demonstrated to work well for HA antigens from influenza, it is likely that the method can also be applied for other HA antigens derived from other viruses, such as measles virus. Thus, the invention relates to a method for separating HA, wherein HA is of an influenza virus or a measles virus. Preferably, the influenza virus is an influenza A virus or an influenza B virus. Also preferred are methods wherein the HA is of an influenza A virus strain comprising an H1, H3, H5, or H7 hemagglutinin. For an accurate calculation of the HA concentration, it is preferred to have the HA0 mature form of influenza substantially separated into the subunits HA1 and HA2, as HA1 is generally the component which can be easily distinguished in chromatograms and of which the peak area can easily be assessed.

The reduction of the antigen is preferably pH controlled, i.e., buffered to a suitable pH. Typically, as described herein, a pH of about 8.0 was applied. However, other suitable (relatively neutral) pH values may be used, such as pH 7. It is important to note that the antigen precipitates in solution at pH values that are too low, for instance at a pH value of 4, or even lower. pH values between about 5 and about 9 may typically be applied, while more preferably values between about 6 and about 8 are applied, since at pH 6 the hemagglutinin antigen unfolds during the infection process under natural conditions. It is most preferred to use a pH value between about 7 and about 8. The person skilled in the art will be capable in finding the correct pH value with which the antigens are still acceptably separated, while it is also readily visible when a pH value is too low as the antigen precipitates at such values. As stated herein, it is well within the skill of the skilled person to adjust pH values and to buffer solutions. Typically, as used herein, a solution is buffered with Tris/HCl, but this is not critical to the invention.

Reduction of the antigen preparation is preferably performed using a reducing agent such as dithiotreitol (DTT). To prevent the antigens from re-association or from complex formation, it is highly preferred to have the sulfhydryl groups protected. This is performed through inert derivatization. Derivatization is preferably performed using an alkylating agent. Alkylation is preferably performed by using IAA. Especially when methods are performed in high throughput setting in which the antigen preparations may be left a prolonged period of time before application on the column, it is preferred to keep the antigens dissociated from each other, and thus to have no active groups present on the proteins.

Alkylation may also be used for regular settings, or short-term methods.

The art discloses the use of an RP-HPLC method to separate influenza virus components (Phelan and Cohen, 1983). In this, viral proteins were solubilized and denatured in guanidine-HCl, and reduced by incubation with DTT for several hours at room temperature, wherein the pH was not controlled. Subsequently, analysis was performed by RP-HPLC at room temperature on a silica-based (C8) Aquapore column, applying a linear gradient of 0.05% TFA in water to 0.05% TFA in acetonitrile. However, the separation of the various virus components was far from optimal, whereas the recovery was low and not quantitative, presumably due to aggregation of the virus components and/or nonspecific adsorption to the HPLC system/column. Alkylation, or any other inert derivatization of the preparation was not applied, which may have resulted in re-association of components and unwanted complexes may have been formed. In addition, in this HPLC assay HA2 could not be detected, presumably because it had been trapped on the column matrix due to its strong hydrophobic nature.

Although the RP-HPLC method is generally quick, the teaching of the art was that it was not suitable for accurate measurements of antigenic determinants, such as HA of influenza. Guanidine-HCl, as used in the art, is a chaotropic agent that seems too harsh for the antigens and may even destroy some of the antigens of interest. Thus, such chaotropic agents are preferably not used for the methods of the invention. Suitable detergents that are typically applied for the invention are for instance SDS and several zwitterionic detergents. Examples of zwitterionic detergents are ZWITTERGENT™ 3-08, 3-10, 3-12 and 3-14 (the 3-14 compound of CALBIOCHEM® is synonym for n-Tetradecyl-N,N-dimethyl-3-ammonio-1-propanesulfonate). The person of skill in the art is able to distinguish which detergents are suitable, as those would provide results with well-separated antigens that may easily be quantified. Unsuitable detergents that would disrupt or even destroy the antigens may just as easily be distinguished, since these would not give proper separated peaks in the chromatograms.

The problem to be solved was to provide an accurate, rapid and robust method, that would be applicable for high-throughput, and that would not have the disadvantages as found in the art. The inventors of the invention have now found that RP-HPLC can nevertheless be used for this purpose and that such columns can be used if the temperature of the column was raised up to (but not including or above) the temperature with which the column material can no longer be used. The inventors have found that the HA antigen, and especially the main determinant HA1 is separated extremely well from the other proteins present in the preparation. This now enables the skilled person to measure the peak of the separated protein in an RP-HPLC chromatogram and to determine the amount present in the preparation, either by comparing it to other (known) values or to internal standards. Preferably, the elution is performed at a temperature above room temperature, typically above approximately 25° C. The inventors have found that values above room temperature are well suited for this purpose. It is also found that temperatures between about 50° C. and about 70° C. are even more suitable for that purpose. Thus, in a preferred embodiment, the invention relates to a method according to the invention, wherein elution is performed at a temperature between about 25° C. and about 70° C., more preferably between about 40° C. and about 70° C., and even more preferably between about 50° C. and about 70° C., most preferably between about 60° C. and about 70° C. The best performance was detected at about 60° C. and about 70° C., which latter value is close to the temperature with which the column material can no longer be applied for proper separation purposes. It is thus also part of the invention to perform the methods of the invention up to the highest temperature possible before the column material does no longer allow proper separation. Typically, most elutions were performed at a temperature of about 65° C. Suitable column materials that are typically used are polymer-based materials. Silica-based materials are less suitable, since they generally do not allow elution at high temperatures. The person skilled in the art of RP-HPLC can easily determine to what temperature certain column materials can be raised before they become useless for the purpose. So, in a highly preferred embodiment, the invention relates to a method according to the invention, wherein elution is performed at a temperature of approximately 60° C., approximately 65° C. or approximately 70° C.

It is to be understood that typical methods of RP-HPLC technology have been applied, and that a person skilled in the art of RP-HPLC and HPLC is well aware of minor adjustments that would not alter the results to be obtained, such as different measurements at other suitable wavelengths or by the use of other column material that would not severely alter the results obtained by the invention.

As mentioned infra, it is a well known fact in the art that the mature influenza antigen HA0 is processed to the sub-fragments HA1, and HA2, upon cleaving with for example trypsin. Since the methods according to the invention use the separation in RP-HPLC such that the HA1 peak is measured for proper and accurate determination of the titer, it is preferred to have full cleavage of the mature protein. This can be achieved by a further step in which a protease compound is added that cleaves most if not all un-cleaved mature protein into the two desired sub-fragments. Typically, but not necessarily, the compound trypsin is used for this purpose. Thus, the invention also relates to a method according to the invention, comprising the further step of incubating the antigen preparation with a protease such as trypsin. This step is suitable for cleaving most if not all remaining un-cleaved mature forms of the HA antigen. Since the trypsin component is preferably removed from the solution before analysis, it is preferred to have the protease such as trypsin present on beads, preferably agarose beads. These beads can easily be removed by centrifugation, after the trypsin has cleaved most, if not all, HA0 into its separate subunits. Clearly, in another setting, one could choose to add trypsin inhibitors after the trypsin has cleaved all HA0, in which case the use of beads is not necessary.

Importantly, it was also noticed by the inventors that upon re-addition of DTT after alkylation, the HA1 recovery seemed to be 6 to 10% higher than after reduction alone. Thus, in one preferred embodiment, a further step is included, wherein the reducing agent is added after alkylation of the reduced antigen in the sample preparation procedure.

Methods described herein now enable one of skill in the art to separate HA1 from other proteins in a very robust, rapid and accurate way. The RP-HPLC chromatograms that are produced in machines applied for the methods of the invention can also be used to determine the peak values of the separated proteins. Since these can be compared to known values of known antigens or to internal values used by the person carrying out the method, one is now able to accurately determine the amount of antigen present in the starting material. Thus, the invention also relates to a method for quantifying the HA titer of an HA antigen preparation, the method comprising the method of separating the HA according to the invention, with the further step of measuring the peak area of the eluted antigen in a chromatogram resulting from the elution step. Preferably, the method of quantifying is applied for influenza antigens; a preferred embodiment relates to a quantification method according to the invention, wherein the HA antigen is of an influenza A virus.

EXAMPLES

The following Influenza A antigens have been used herein (NIBSC-reference numbers underlined):
A/New Caledonia/20/99 (H1N1) 00/608
A/Duck/Sing (H5N3) 00/522
A/Panama/2007/99 (Resvir-17; H3N2) 02/100
A/Equine/Prague/56 (H7N7) 85/553

All influenza antigens were obtained from the National Institute for Biological Standards and Control (NIBSC, Hertfordshire, United Kingdom). The antigen A/Panama/2007/99 (D953-043F) was also produced using PER.C6® (immortalized, human embryonic retinoblast cell)-based technology.

Example 1

Determination of Hemagglutinin in Influenza Preparations of A/Panama/2007/99 (Resvir-17; H3N2) Using Reversed Phase HPLC The egg-derived influenza antigen preparation A/Panama/2007/99 (Resvir-17; H3N2) from NIBSC and the same antigen produced on PER.C6® (immortalized, human embryonic retinoblast cell)-based technology, were analyzed on Reversed Phase-HPLC (RP-HPLC).

The production of antigen produced on PER.C6 cells (immortalized, human embryonic retinoblast cells) was performed as follows: PER.C6® cells (immortalized, human embryonic retinoblast cells) (as represented by the Human embryonic retina (HER) cells under ECACC no. 96022940 deposited with the European Collection of Cell Cultures (ECACC) at the Centre for Applied Microbiology and Research (CAMR), Salisbury, Wiltshire, UK) were cultured in a bioreactor (37° C., DO=50%, pH 7.3) until a viable cell density of $1 \times 10^6$ cells/ml was accomplished. The cells were infected with influenza viruses of the strain Resvir-17 (H3N2) (35° C., with a multiplicity of infection of $1 \times 10^{-4}$) in the presence of 3 µg/ml trypsin/EDTA. The infection was continued for 5 days. The bioreactor content was then treated with 10 U/ml benzonase (Merck) for 30 minutes at 37° C. This was followed by clarification with a 3.0 µm filter (Clarigard, Millipore) and a ten-fold concentration step, using tangential flow filtration (Hollow-fiber module, Amersham). Subsequently, the product was applied on sucrose gradient from 10 to 42% in PBS and centrifuged for 2 hours at 22,000 rpm in an ultracentrifuge (Beckman). The virus band was visible by the eye and was collected using a syringe. This material was used for development of the HPLC method.

Both batches of Resvir-17 antigen were disintegrated by addition of SDS (Gibco BRL) to a final concentration of 1% (w/v), and reduced with 60 mM DTT in 0.15 M Tris, pH 8.0, for 30 minutes at 65° C. After cooling down, reduced proteins were alkylated by incubation with iodacetamide (IAA, final concentration of approximately 106 mM) at 37° C. for 45 minutes in the dark. This alkylation step prevents the released proteins with free reactive sulfhydryl groups (e.g., HAL HA2, and NA) from associating with each other.

Analysis was performed on an Agilent 1100 HPLC system with 900 µl loop injector, using a polystyrene dimethylbenzene POROS R1/10 (2.1×100 mm) Reversed Phase column (Applied Biosystems), and the gradient profile described in Table 1. Proteins were detected with a multiple wavelength detector at 215 nm.

Between 50-300 µl of sample was injected (approximately 10 µg HA as determined by SRID), and RP-HPLC was performed with a flow of 0.8 ml/min and at a column temperature of 70° C.

The RP-HPLC assay according to the invention for quantification of the HA titer in influenza virus preparations is based on measuring the peak area of its subunit HA1. The protein is solubilized upon addition by detergent, submitted to reduction/alkylation with DTT/IAA (respectively), and subsequently analyzed utilizing the RP-HPLC procedure according to the schedule depicted in Table 1. As a consequence, a crucial parameter of the assay is the selectivity, i.e., the resolution between the HA1 peak and other virus-derived material in a Reversed Phase chromatogram. The person skilled in the art is aware of the fact that the organic mobile phase may be performed with different agents. Typically, acetonitrile is used as solvent B (see Table 1). Other solvents B that may be used are methanol, isopropanol and ethanol. As part of solution A and B (see Table 1) an anionic or cationic ion-pairing agent is typically used. Examples of anionic ion-pairing agents that may be used in the methods of the invention are trifluoracetic acid (TFA), pentafluoropropionic acid (PFPA) and heptafluorobutyric acid (HFBA) and the like. Examples of cationic ion-pairing agents that may be used in the methods of the invention are tetramethylammonium chloride, tetrabutylammonium chloride and triethylamine.

The selectivity of the assay was explored first by analyzing formaldehyde-inactivated influenza A subtype Resvir-17 (H3N2) produced in chicken eggs at the NIBSC (FIG. 1). A total amount of Resvir-17 antigen corresponding to 10.0 µg HA was injected, and analyzed applying the acetonitrile gradient described in Table 1. The peak fractions as depicted in FIG. 1 were collected, and vacuum-evaporated for 45 minutes at 30° C. to remove most acetonitrile from the samples. Subsequently, the fractions were concentrated on Microcon YM-10 filter devices (Amicon) according to the manufacturer's protocol, taken up in lithium dodecyl sulfate sample buffer (LDS, Invitrogen), and analyzed by SDS-PAGE, silver staining and Western blot analysis to determine which fraction contained HA1. SDS-PAGE was carried out with NuPAGE 4-12% Bis-Tris gels (Invitrogen) at a constant voltage of 200 V for 55 minutes. Proteins were stained utilizing the SilverXpress® silver staining kit (Invitrogen) according to the corresponding instruction manual. HA proteins and/or fragments were detected by Western blot analysis, using an antiserum from sheep raised against partially purified HA of A/Panama/2007/99 (H3N2) (NIBSC, catalogue no. 02/338). For this purpose, the proteins analyzed on SDS-PAGE gels were blotted onto PVDF membranes (Millipore) for 1.5 hours at 20 V. Next, the membranes were incubated for 1 hour in blocking buffer (5% (w/v) non-fatty milk powder (BioRad) in TBST), for 1 hour in blocking buffer, containing the sheep anti-HA antiserum at a final dilution of 1:500, and finally in blocking buffer, containing rabbit anti-sheep horse radish peroxidase conjugate (Rockland, USA) at a final concentration of 1:6000. According to the instruction manual, ECL Western blotting reagents (Amersham) were used to detect the HA antigens.

Figure 2:
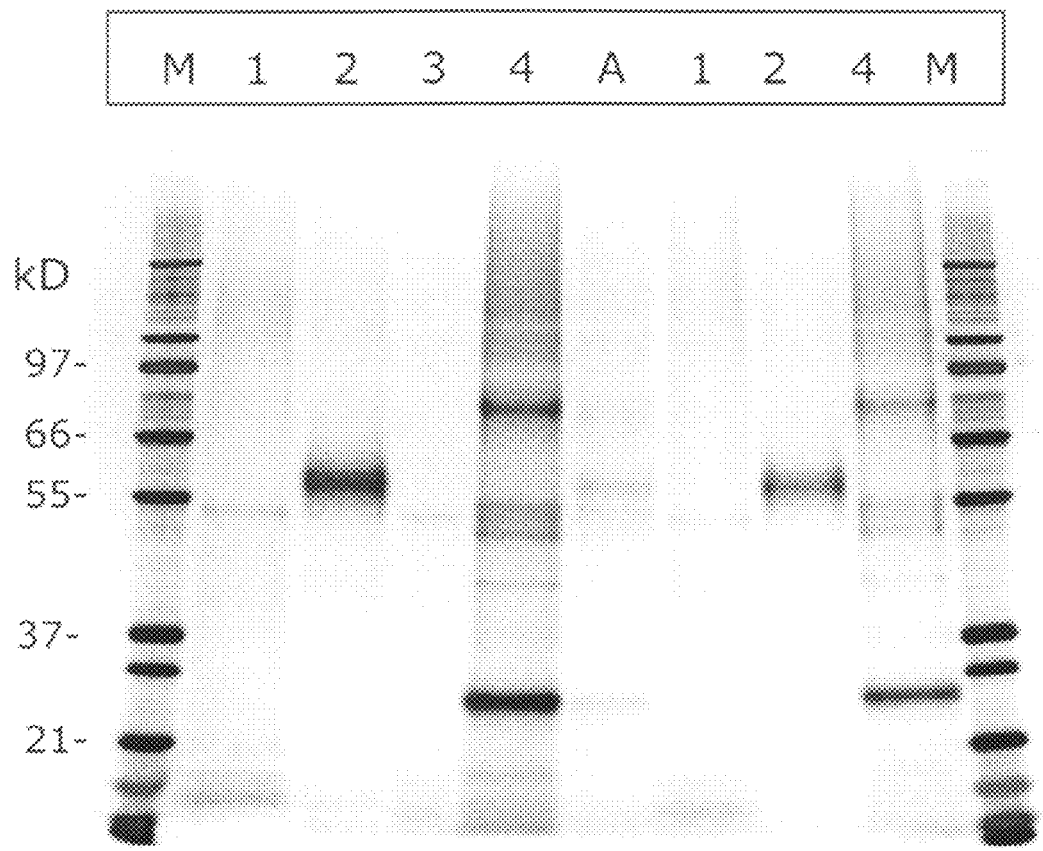
FIG. 2. SDS-PAGE silver staining of the four RP-HPLC fractions of FIG. 1. A=antigen control. Fraction 1 is the flow through. M=kD size marker.
Figure 3:
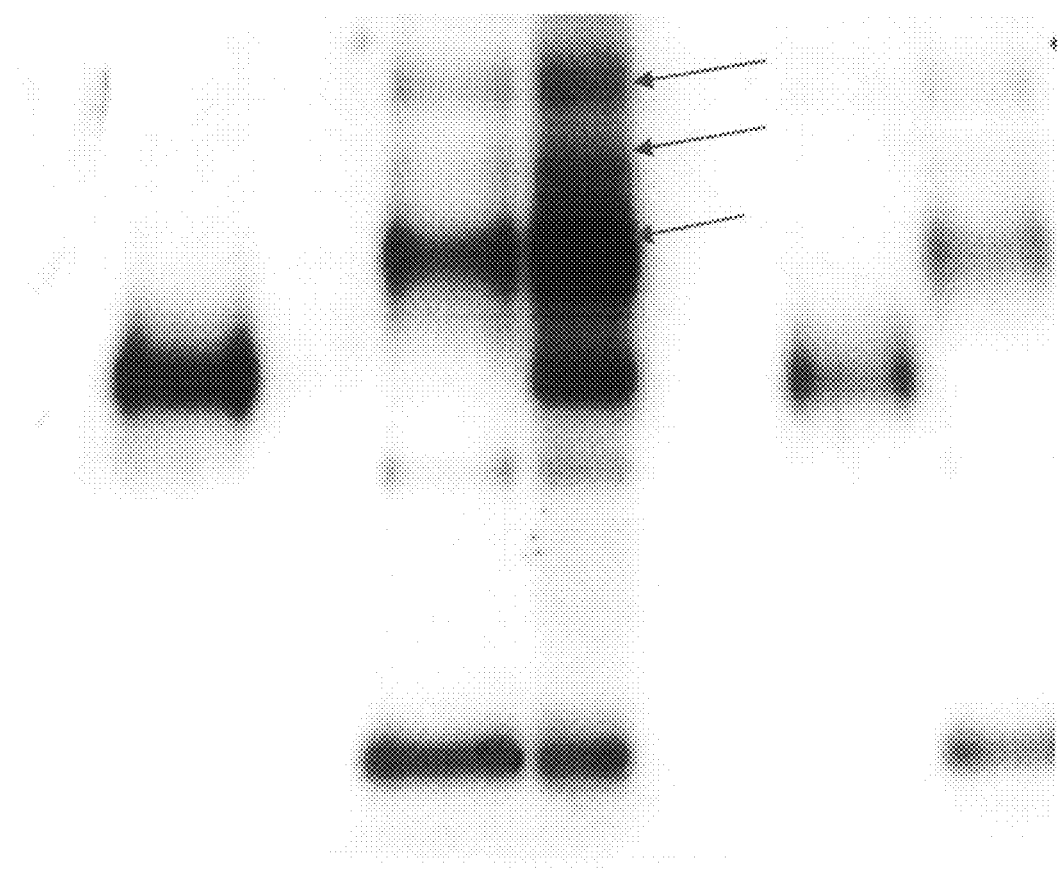
FIG. 3. Western blot analysis (anti-HA) of the four RP-HPLC fractions of FIG. 1. A=antigen control. Fraction 1 is the flow through. The arrows indicate forms of HA antigen that was not cleaved before application on the column.

The results of the silver stained SDS-PAGE gel are shown in FIG. 2. Apparently, the first peak with a retention time of about 8.9 minutes (fraction 2 in FIG. 1) contained all detectable HA1 (molecular weight of approximately 55 kDa), while being barely, if at all, contaminated with other proteins (FIG. 2, lane 2). Western analysis confirmed that the 55 kDa band indeed contained HA1, as this band was clearly recognized by the anti-HA antiserum (FIG. 3, lane 2). Interestingly, in the starting material prior to the injection on the HPLC (FIG. 3; lane A, which indicates the loaded antigen without purification over the column) a triplet of immunoreactive bands was visualized, most likely representing the intact monomeric, dimeric, and trimeric forms of HA, and therefore indicating that a substantial part of HA was resistant to cleavage into HA1 and HA2. Complete cleavage is a prerequisite for an accurate quantification of HA samples. If it is unsure whether all HA0 has been fully cleaved, it is thus preferred to have the HA fully cleaved by a protease before loading. This issue is further addressed below, in example 7. Arrows in FIG. 3 indicate the multimeric forms. This phenomenon has most likely been caused by the formaldehyde treatment of the antigen preparation, by which proteins together in a complex (like trimeric HA) are partly irreversibly cross-linked. As demonstrated in FIG. 3 (lane 4, corresponding to fraction 4 the in RP-HPLC of FIG. 1), these cross-linked HA forms eluted separately from the HA1 form that eluted predominantly in fraction 2.

Figure 4:
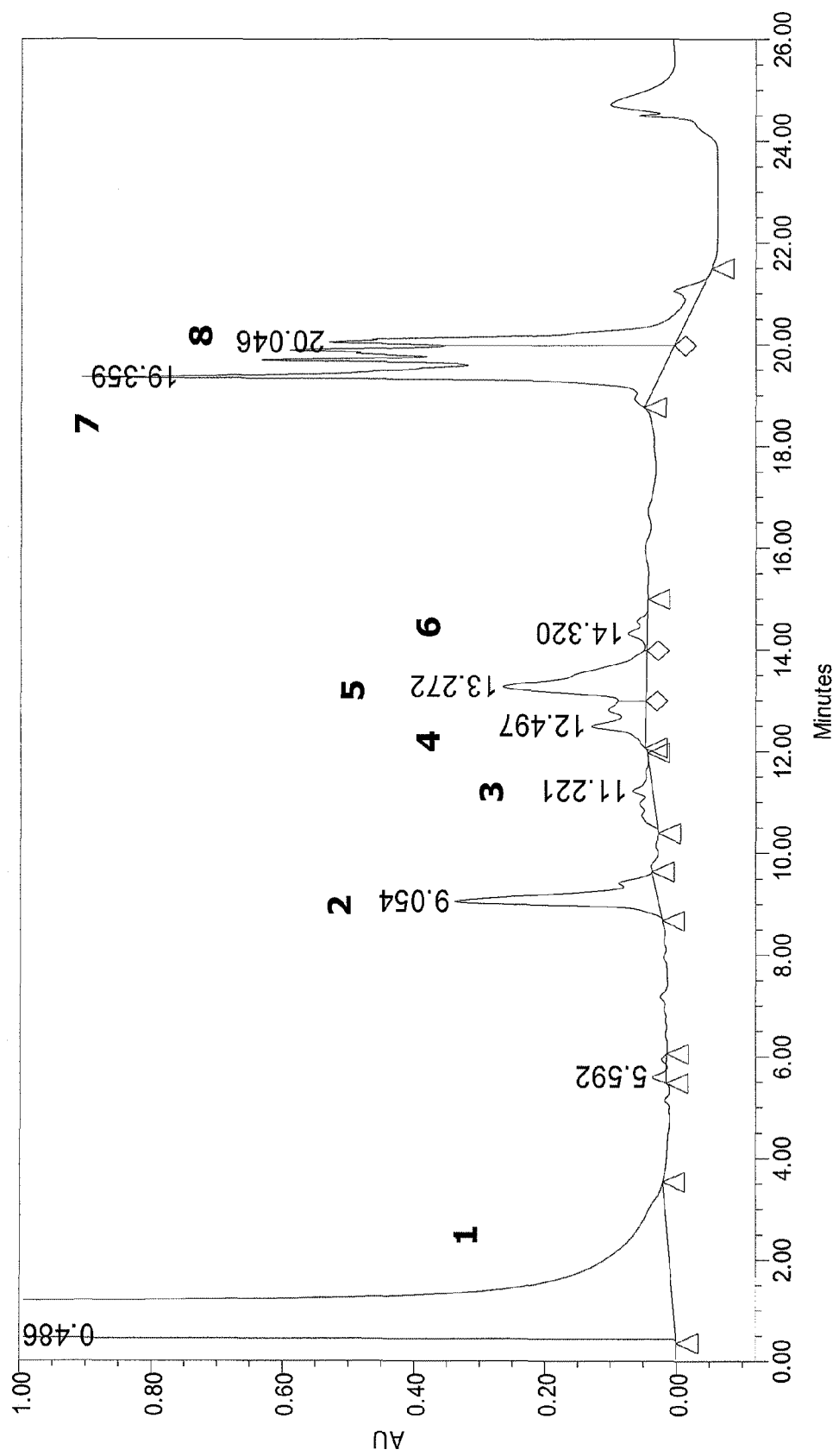
FIG. 4. Reversed-Phase HPLC of PER.C6® (immortalized, human embryonic retinoblast cell) produced, reduced and alkylated influenza A/Panama/2007/99 (Resvir-17; H3N2). An amount corresponding to 16.6 µg HA (as determined by SRID) was injected. Numbers 1-8 correspond to the fractions applied on SDS-PAGE of FIG. 5.
Figure 5:
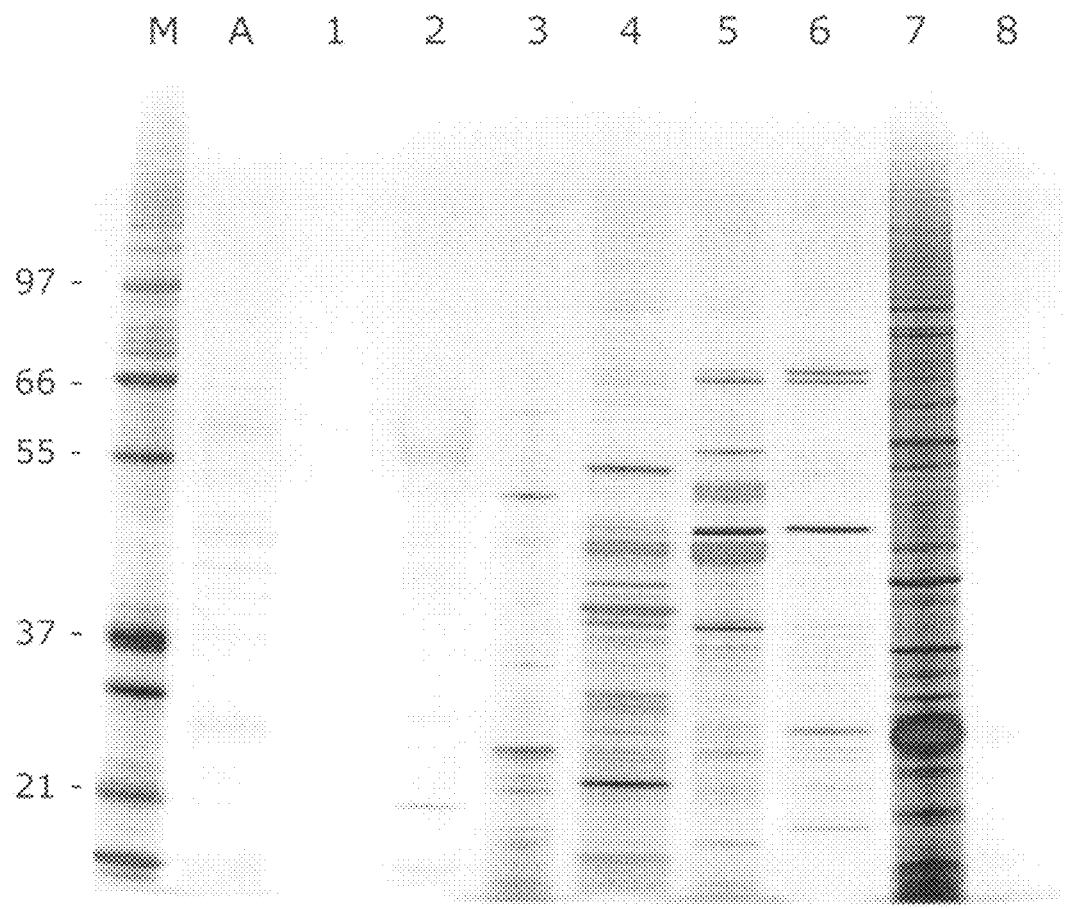
FIG. 5. SDS-PAGE silver staining of the eight RP-HPLC fractions of FIG. 4. A=antigen control. Fraction 1 is the flow through. M=kD size marker.

PER.C6® (immortalized, human embryonic retinoblast cell)-produced Resvir-17 antigen material was also analyzed by RP-HPLC (FIG. 4). This virus preparation was inactivated by beta-propiolactone (BPL) treatment, which in principle does not affect the characteristics of the viral proteins. In FIG. 4 the total amount of HA injected was approximately 16.6 µg. RP-HPLC analysis was performed utilizing the gradient profile as depicted in Table 1. Again, the peak fractions as denoted in FIG. 4 (eight in total) were collected, and prepared for SDS-PAGE, silver staining and Western blot analysis as already described in this section for egg-produced Resvir-17 antigen (FIGS. 2 and 3, respectively). It appeared that, in addition to the influenza virus encoded proteins, the PER.C6® (immortalized, human embryonic retinoblast cell)-produced batch of Resvir-17 antigen contained several other proteins (FIG. 5, lane A, which indicates the antigen before application on the column), most likely representing host cell proteins. This was also reflected by the RP-HPLC chromatogram of this batch, showing numerous peaks eluting between 10 and 15 minutes (FIG. 4, peaks denoted as 3-6).

Figure 6:
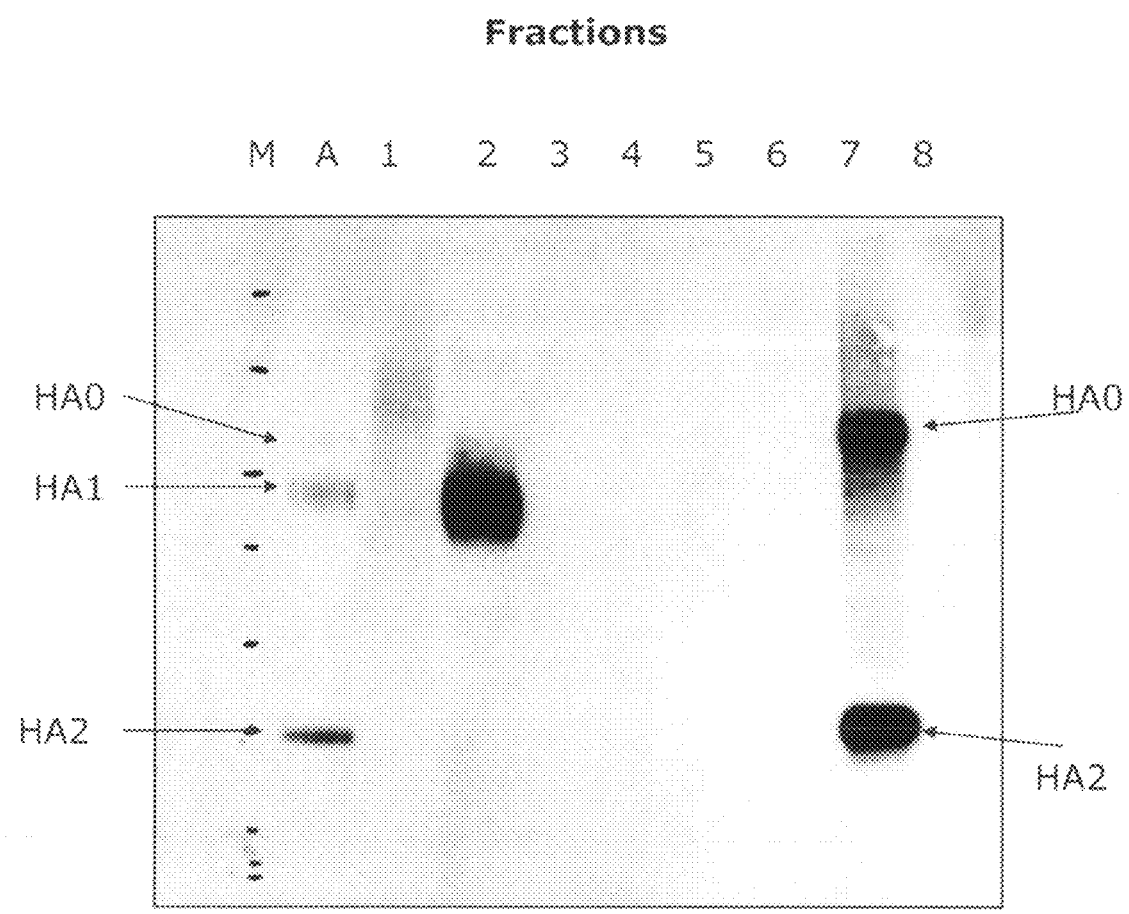
FIG. 6. Western blot analysis of the eight RP-HPLC fractions of FIG. 4. A=antigen control. Fraction 1 is the flow through. M=kD size marker. HA0=the mature antigen. HA1 and HA2=cleaved hemagglutinin antigens.

Nevertheless, the first peak with retention time of around 9 minutes (FIG. 4), contained HA1 as demonstrated by the SDS-PAGE silver staining and Western blot analysis of the HPLC peak fractions (FIGS. 5 and 6, lanes 2), was well-resolved from other protein peaks, which shows that the methods are also very useful for methods in which the antigens are produced on tissue culture cells.

Consequently, these data indicate that the assay selectivity, i.e., the separation of HA1 with the other viral components in both egg- and PER.C6® (immortalized, human embryonic retinoblast cell)-derived H3N2 Resvir-17 antigens, was excellent.

Example 2

Determination of Hemagglutinin in Influenza Preparations of A/Duck/Sing (H5N3) and A/New Caledonia (H1N1) using Reversed Phase HPLC Further, it was investigated whether the RP-HPLC assay was also applicable for hemagglutinins from other influenza A subtypes. Hence, the selectivity of the assay with two other influenza A subtypes, A/Duck/Sing (H5N3) and A/New Caledonia (H1N1) was determined.

Figure 7:
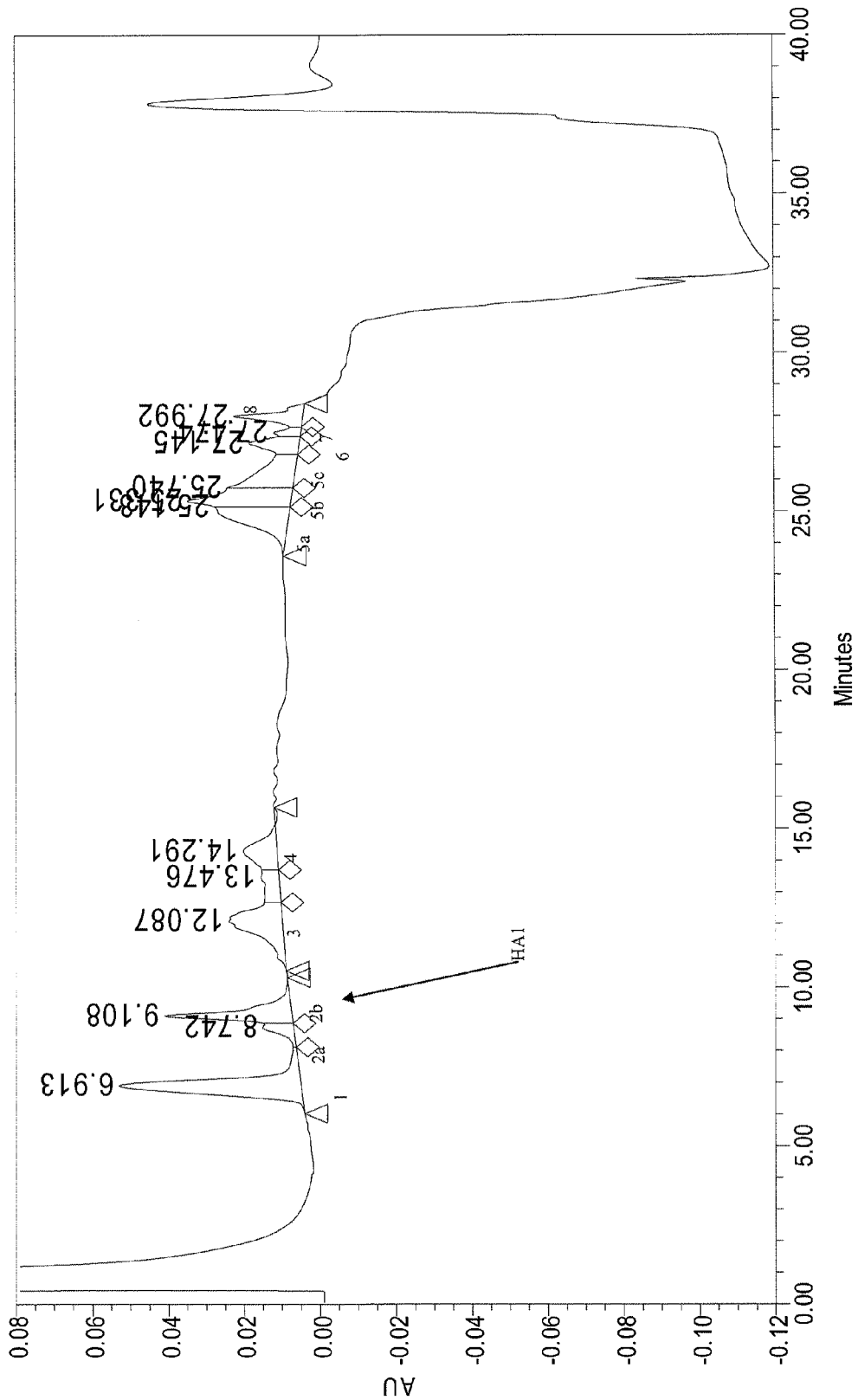
FIG. 7. Reversed-Phase HPLC of egg-derived, reduced and alkylated influenza A/Duck/Sing (H5N3) 00/522. An amount corresponding to 3.0 µg HA (as determined by SRID) was injected. The numbers 1, 2a, 2b, 3, 4, 5a, 5b, 5c, 6, 7 and 8 refer to fractions, with significant peaks, some of which were applied on SDS-PAGE as shown in FIG. 8.
Figure 8:
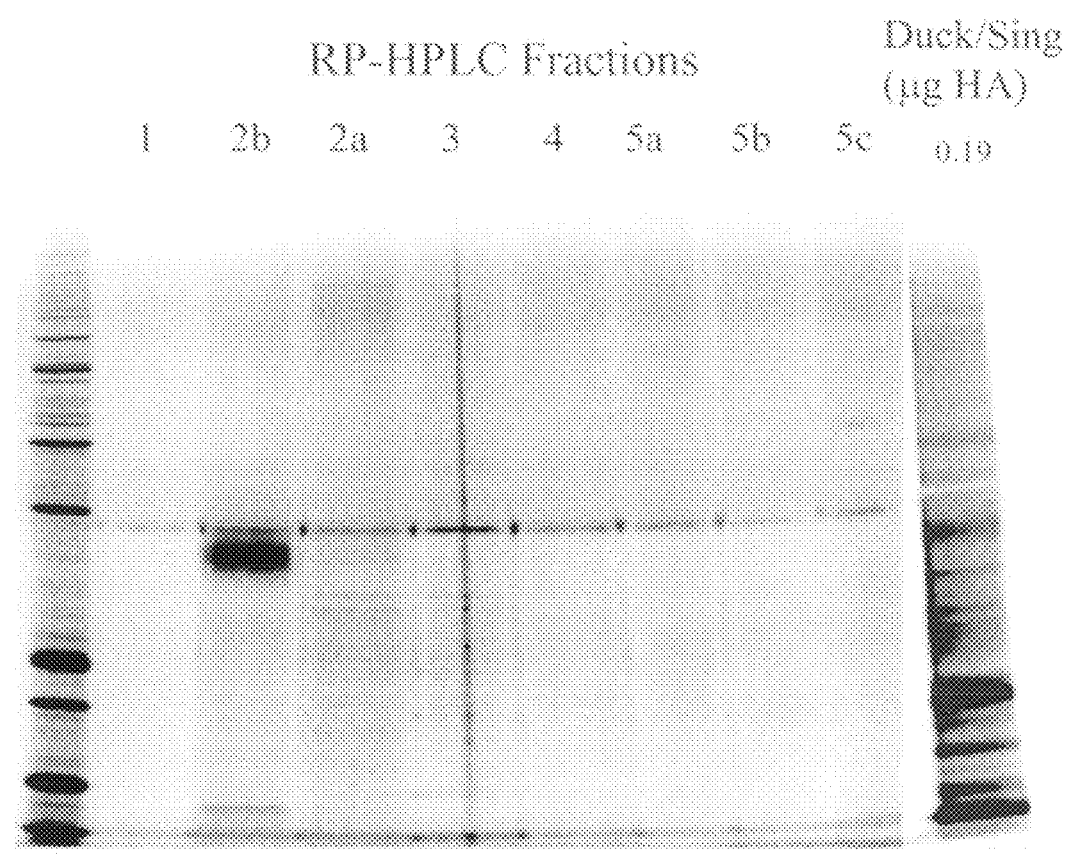

First, an RP-HPLC was performed on egg-derived and formaldehyde-treated H5N3 from A/Duck/Sing. For this an amount corresponding to 3.0 µg HA was injected. Further procedures were as described in example 1, except that instead of SDS, Zwittergent 1% (w/v) was used as the detergent. In FIG. 7, a Reversed Phase chromatogram of the reduced/alkylated H5N3 antigen is shown. SDS-PAGE and subsequent silver staining (FIG. 8) of the proteins demonstrated that fraction 2b contained most, if not all HA1 (Lane 2b). Notably, peak 1 (lane 1 in FIG. 8), although eluting first after the flow through, did not contain HA proteins; hardly any proteins were discernible in this fraction in SDS-PAGE. An amount of 0.19 µg HA antigen that was not applied on the column was taken as a positive control (lane Duck/Sing).

Figure 9:
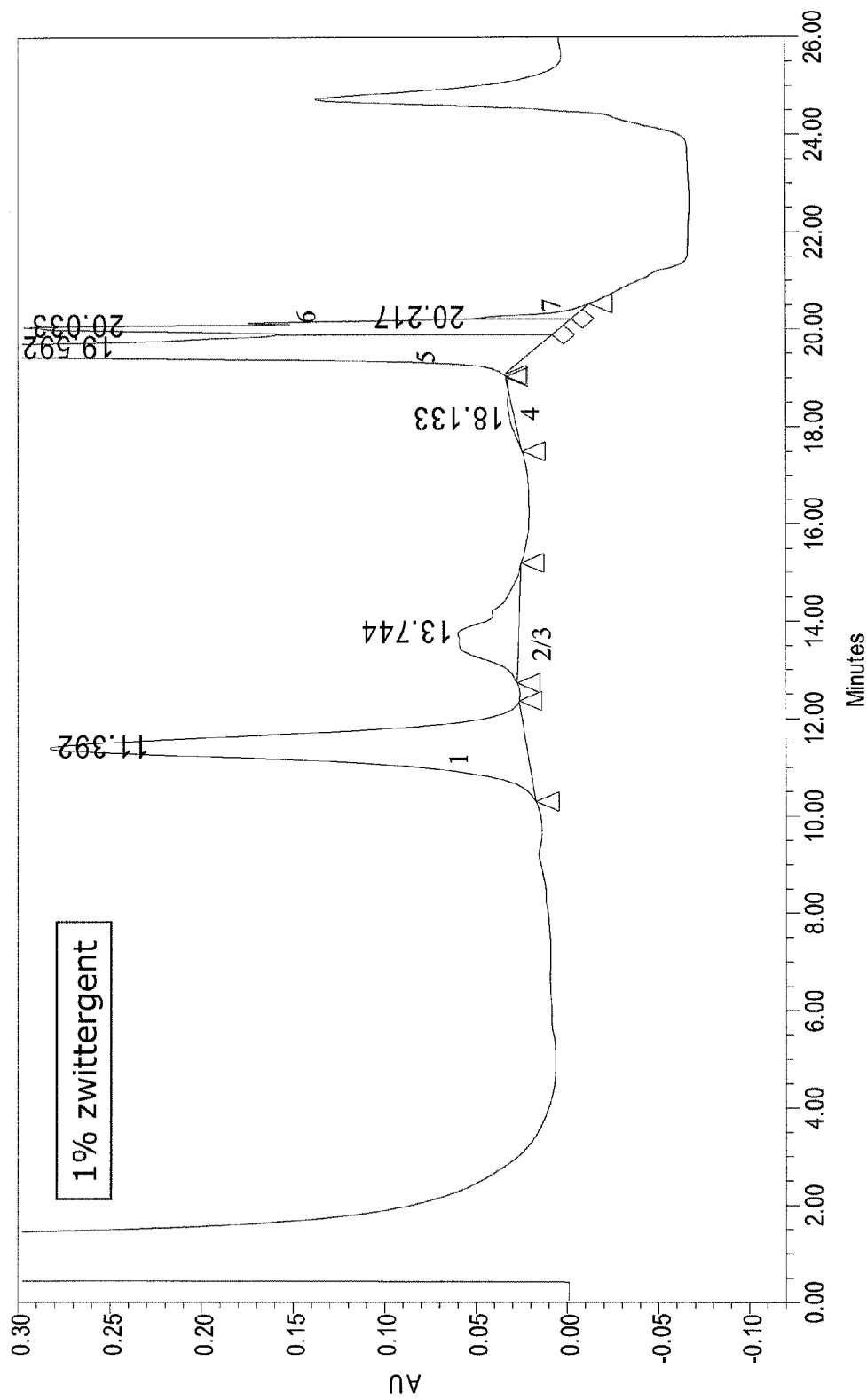
FIG. 9. Reversed-Phase HPLC of egg-derived reduced and alkylated influenza A/New Caledonia/20/99 (H1N1) 00/608. An amount corresponding to 15.0 µg HA (as determined by SRID) was injected. Numbers 1-7 correspond to the fractions applied on SDS-PAGE of FIG. 10.
Figure 10:
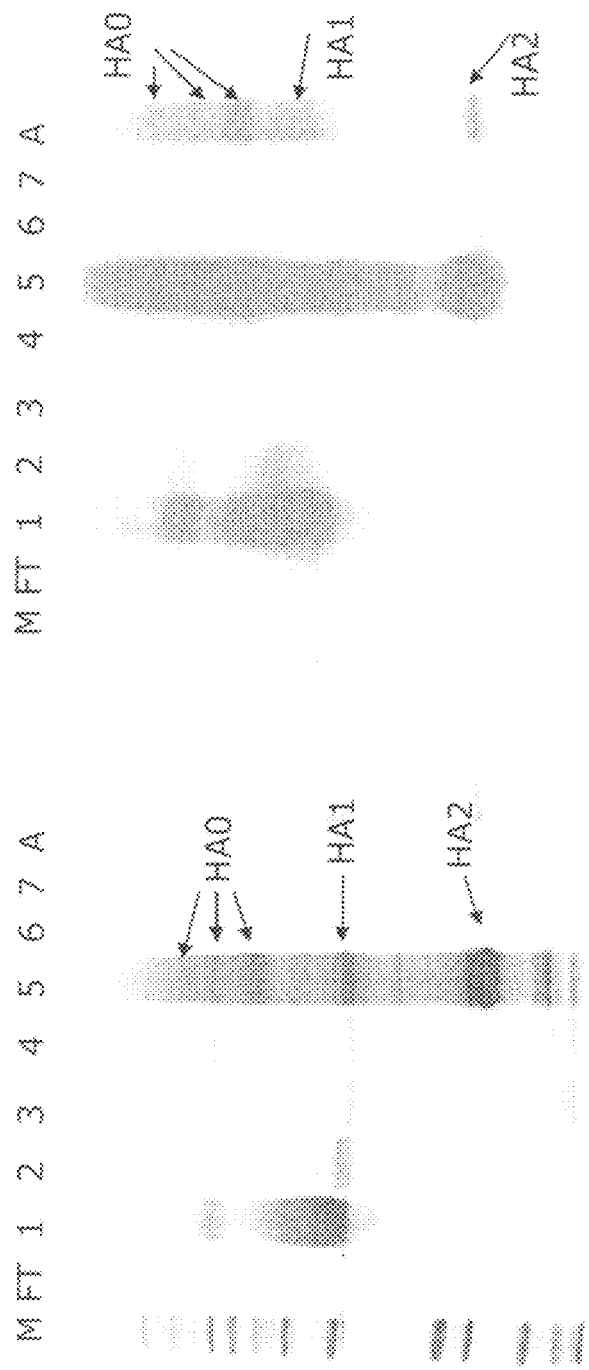
FIG. 10. SDS-PAGE silver staining (left panel) and Western blot analysis using an anti-H1N1 antibody (right panel) of the seven RP-HPLC fractions of FIG. 9. FT=Flow Through. A=antigen, positive control. M=kD size marker. HA0, HA1 and HA2 are indicated by arrows.

A graph of the RP-HPLC of egg-derived, reduced and derivatized influenza A subtype H1N1 (A/New Caledonia) is shown in FIG. 9. An amount corresponding to 15 µg HA was reduced and alkylated under non-buffered conditions, injected on the HPLC, and subsequently analyzed running the acetonitrile gradient presented in Table 1. Further procedures were as described in example 1, except that ZWITTER-GENT™ 1% (w/v) was used as the detergent. The first peak (denoted as 1) with a retention time of about 11.4 minutes, contained predominantly HA1, as shown by silver staining (FIG. 10, left panel) and Western blot analysis (FIG. 10, right panel). The retention time of approximately 11.4 minutes differed significantly from the retention time of the HA1 peak of A/Resvir-17 (FIG. 1), which was about 8.9 minutes. HA1 of A/Resvir-17 has a higher polarity (more hydrophilic) than its counterpart of influenza A/New Caledonia, probably due to the difference in amino acid content. Again, since this antigen batch had also been inactivated by formaldehyde treatment, not all HA0 could be cleaved into its subunits, and, hence, a part of HA0 apparently migrated as uncleaved and multimeric forms in the gel (FIG. 10, right panel, lanes 5 and A, indicated by arrows).

Taken together, these data demonstrate that the assay selectivity for quantification of HA1 is excellent, and in addition, that the RP-HPLC assay is not specific for a particular influenza A subtype, but that it can be applied broadly for different types of influenza viruses.

Example 3

RP-HPLC Assay Linearity for Quantification of Ha of Egg-Derived Influenza a Subtype H3N2

Figure 11A:
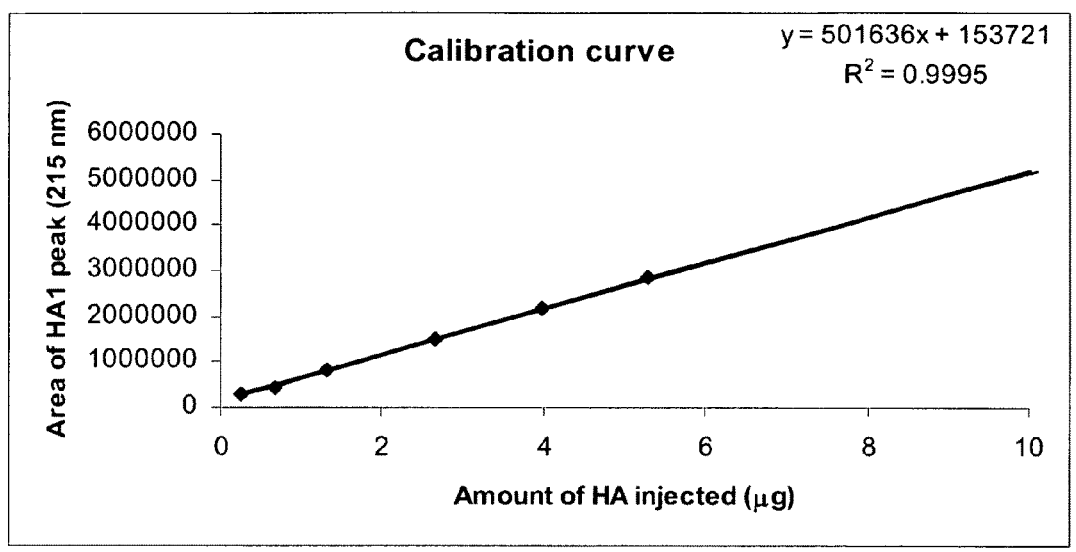
FIG. 11. Linearity study: (A) calibration curve by plotting the measured HA1 peak area versus the injected amount of HA from formaldehyde-inactivated, egg-derived, reduced and alkylated Resvir 17 antigen. (B) idem, now for a PER.C6® (immortalized, human embryonic retinoblast cell)-derived BPL-inactivated A/Resvir-17 sample.

One of the key criteria of an analytical procedure is linearity, the ability (within a certain range) to obtain test results, which are directly proportional to the concentration (amount) of analyte in the sample. Assay linearity was studied with egg-derived, formaldehyde-inactivated, reduced and alkylated influenza antigen from A/Panama/2007/99 (A/Resvir-17; H3N2). Increasing concentrations of HA were injected on the RP-HPLC system with a constant injection volume of 200 µl, and subsequently plotted versus the measured area of the HA1 peak, resulting in a calibration curve as shown in FIG. 11A. It is evident from the data in FIG. 11A, that the assay linearity in the range between 0.3 and 10.6 µg HA injected was very good, as indicated by a correlation coefficient ($R^2$) of more than 0.99. In principle, the real working range is also determined by the accuracy of the HA concentration of the calibration samples measured by utilizing the calibration curve. In a so-called residual analysis, in which the deviation of the actual data points from the regression line (calibration curve) was calculated, it was revealed that the percentage deviation (experimental from predicted HA1 area) for most data points was smaller than 5%. Accepting ±15% difference, in this particular experiment no data points of the curve had to be left out, and, hence, the actual operating range to determine the HA titer was limited between 0.3 and 10.6 µg HA injected.

Figure 11B:
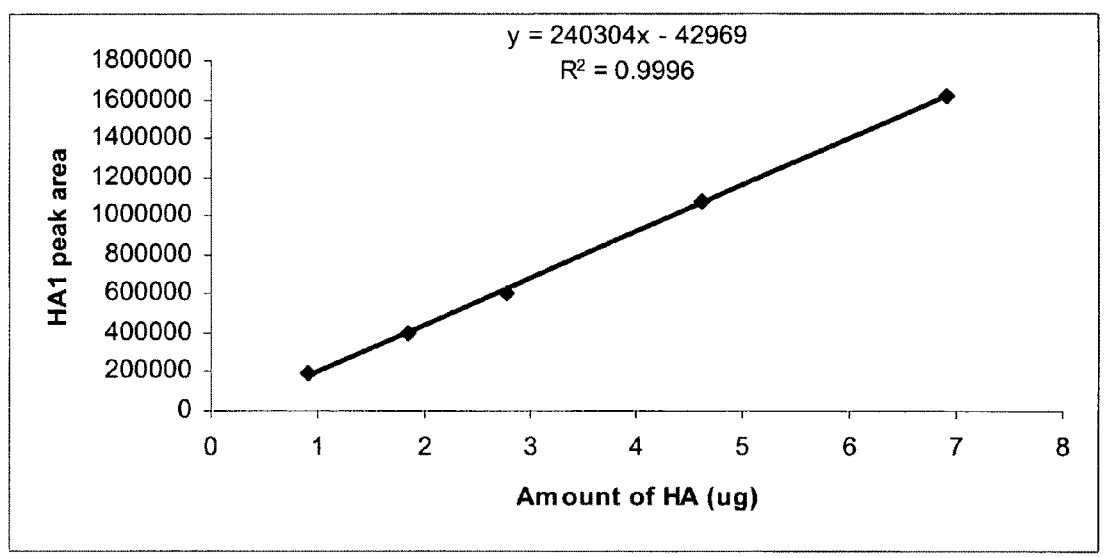

As an important conclusion, as discussed infra, the HA titer of formaldehyde-inactivated influenza samples like the one used above cannot be determined to the highest possible accuracy. Moreover, in the linearity study just discussed sample preparation had not been optimal. Taking these two points into account, linearity was, therefore, also studied with a PER.C6® (immortalized, human embryonic retinoblast cell)-derived but BPL-inactivated A/Resvir-17 sample. The data showed that for the BPL-inactivated influenza A/Resvir-17 sample good assay linearity could be achieved (FIG. 11B).

Example 4

RP-HPLC Assay Precision

Assay precision was studied by analyzing six injections of a reduced and alkylated sample of A/New Caledonia (H1N1) at a relatively low concentration (0.65 µg HA per injection). In addition, precision was also explored by injecting four independently reduced and alkylated samples with a relatively high HA titer (about 3 µg HA per injection). Results are shown in Tables 2 and 3, and demonstrate that the precision was good for both sets of samples with CVs below 10%.

Example 5

Effect of Column Temperature on RP-HPLC Assay Performance of Egg-Derived Resvir-17 Antigen (H3N2)

The effect of column temperature on the assay was also studied. In this respect, egg-derived Resvir-17 (H3N2) antigen was reduced and alkylated as described above, except that these reactions were conducted under non-buffered conditions. Subsequently, samples (approximately 4.3 µg HA per injection) were analyzed at the following column temperatures: 25° C., 40° C., 50° C., 60° C., and 70° C., using the acetonitrile gradient in an organic mobile phase as described in Table 4.

Figure 12A:
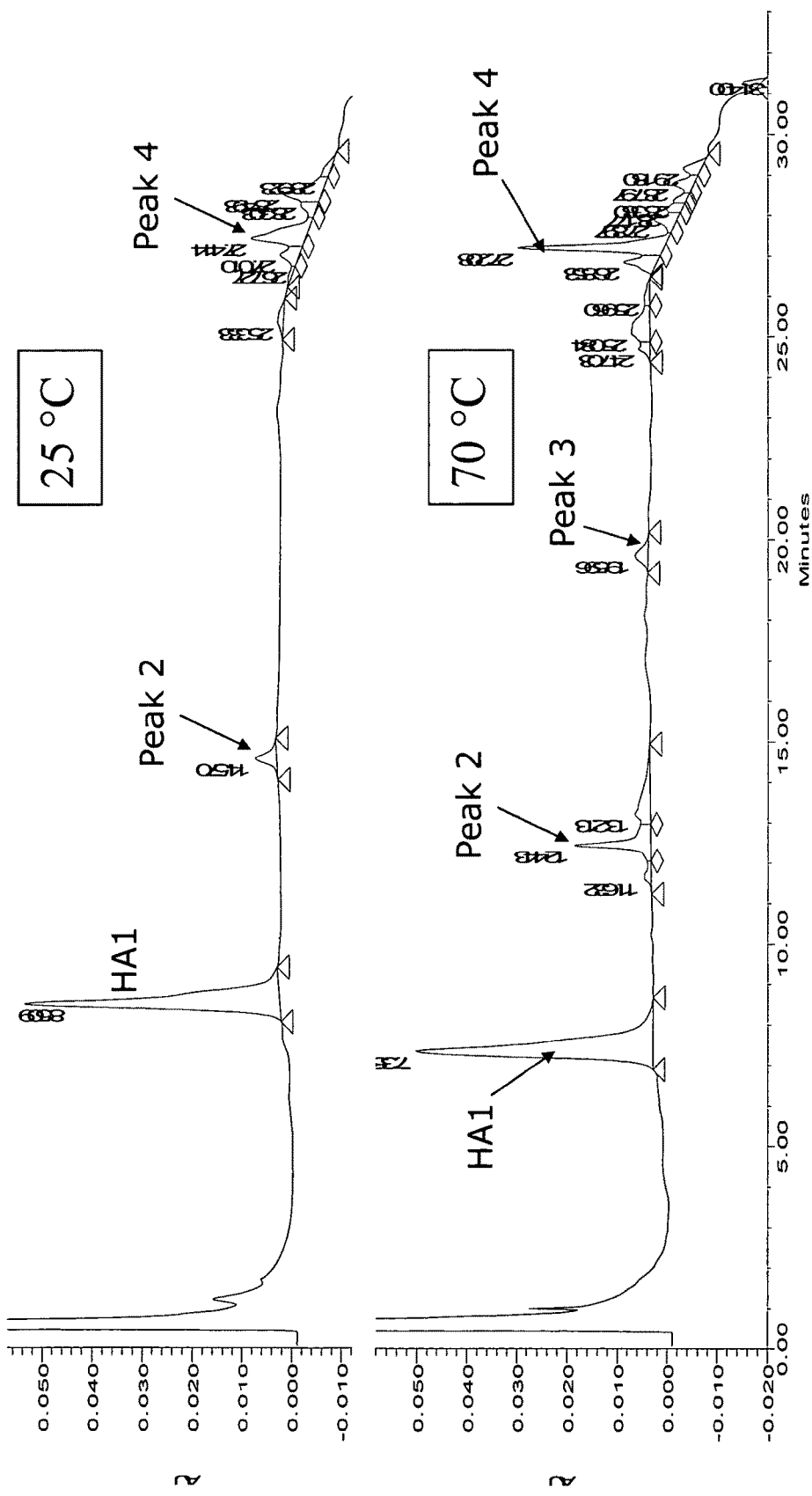
FIG. 12. (A) Reversed Phase-HPLC chromatograms of egg-derived, reduced and alkylated Resvir-17 antigen obtained with column temperatures of 25° C. (upper panel) and 70° C. (lower panel). (B) Effect of column temperature on the recovery (peak area) of HA1 from PER.C6® (immortalized, human embryonic retinoblast cell)-based influenza A/Resvir-17 (dark bars) and A/New Caledonia (light bars).

In FIG. 12A the chromatograms of column temperatures 25° C. and 70° C. are compared. It is evident that the recovery of all peaks was higher at a column temperature of 70° C. In Table 5, the peak areas of HA1 and three other peaks, which were denoted in FIG. 12A (lower panel) as Peak 2, 3 and 4 and which were in general also obtained after RP-HPLC at the column temperatures mentioned above, are presented. Peak 3 could not be distinguished at a column temperature of about 25° C. and about 40° C. It is herein demonstrated that for optimal recovery of HA1 the column temperature range is preferably above about 25° C., more preferably above about 40° C. and most preferably above about 50° C., whereas for recovery of the other three peaks it is preferred to use a column temperature of approximately 70° C. The results as shown in Table 5 show that the most preferred temperature range of the column is between about 50° C. and about 70° C., while the best results were achieved with a temperature of approximately 60° C.

Figure 12B:
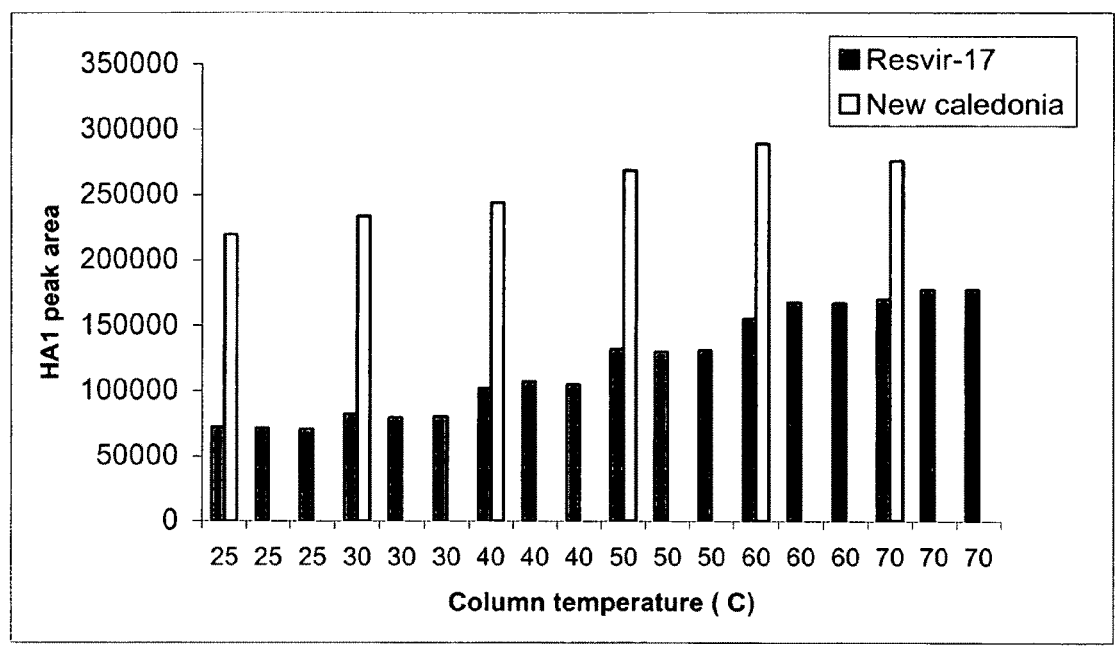
Figure 13:
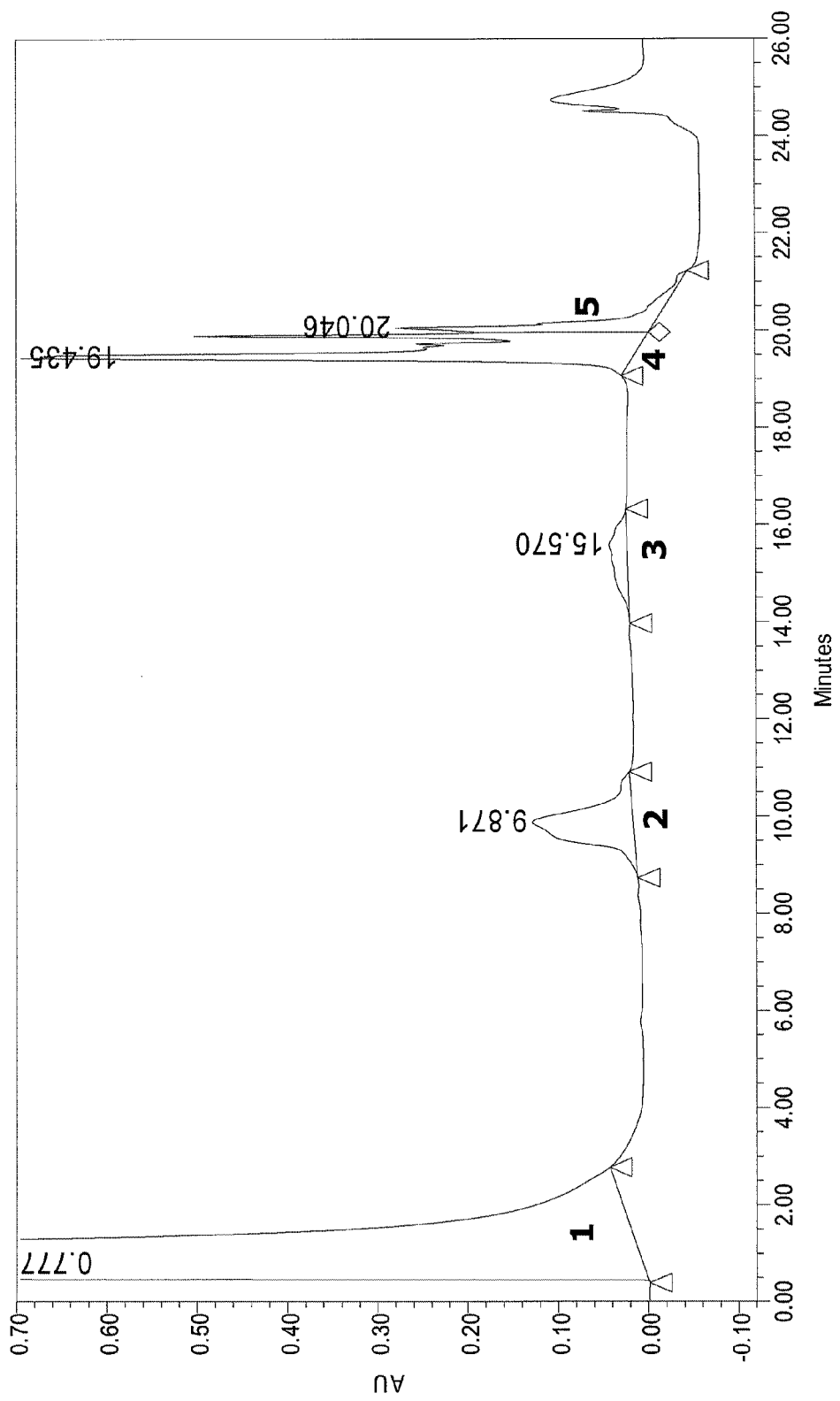
FIG. 13. Reversed Phase-HPLC chromatograms of egg-derived, reduced and alkylated influenza A/Equine/Prague/56 (H7N7) 85/553 antigen. Numbers 1-5 correspond to the fractions applied on SDS-PAGE of FIG. 14.
Figure 14:
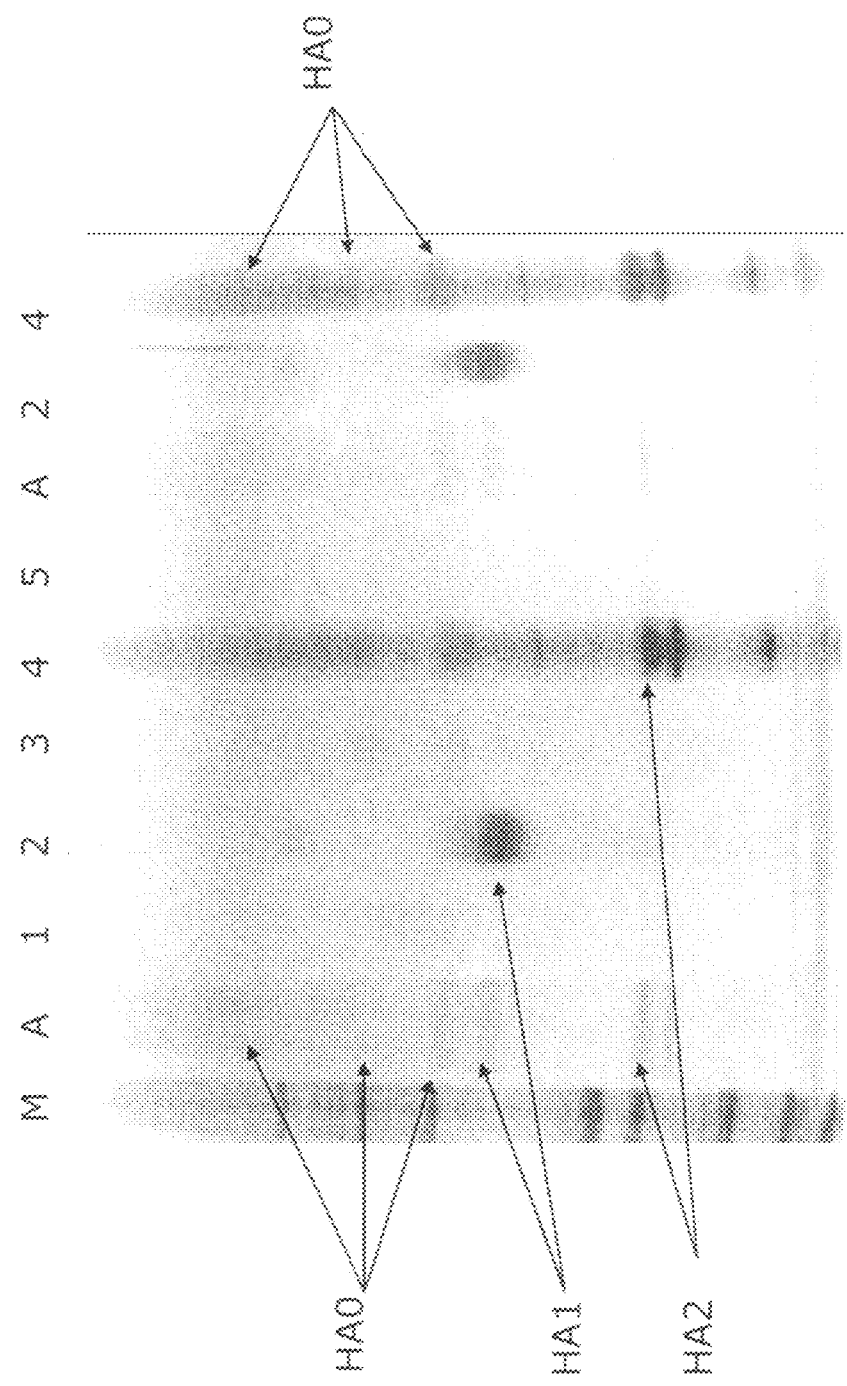
FIG. 14. SDS-PAGE silver staining of the RP-HPLC fractions 1-5 and loaded antigen of FIG. 13. M=size marker. HA0, HA1 and HA2 are indicated by arrows.
Figure 15:
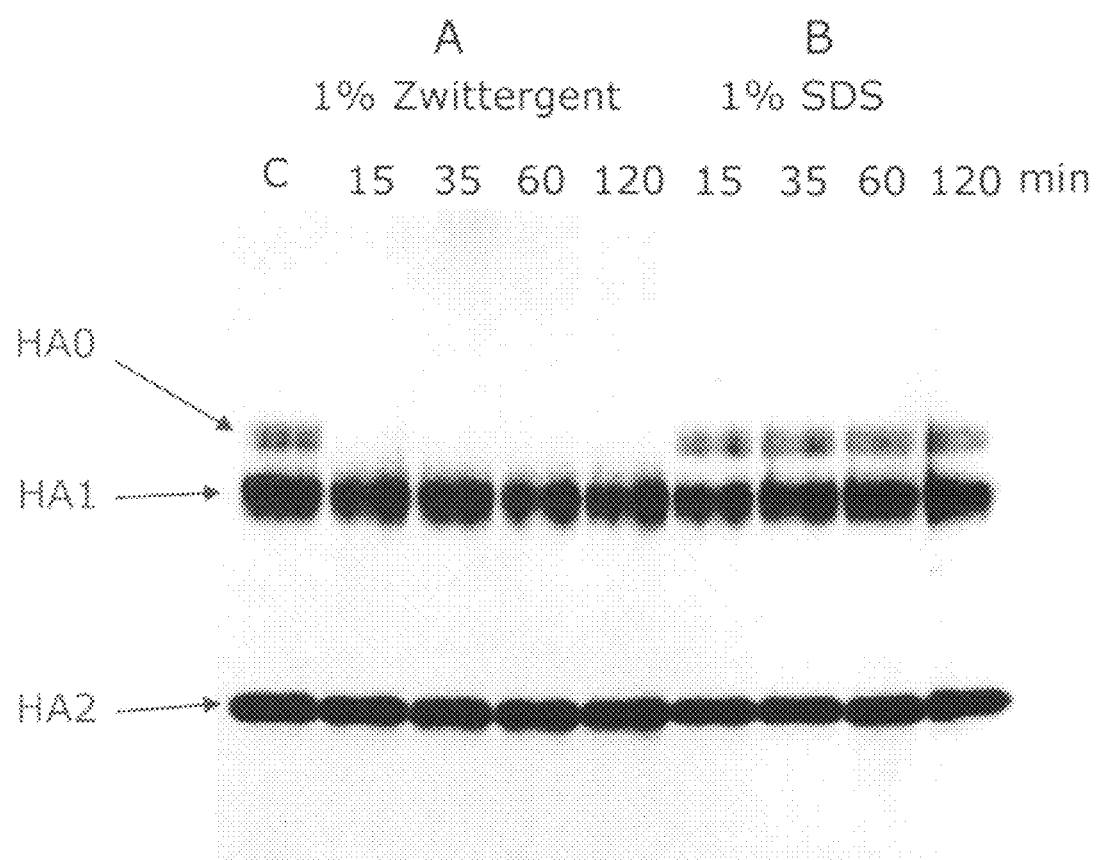
FIG. 15. Western blot analysis of BPL-inactivated PER.C6® (immortalized, human embryonic retinoblast cell)-based A/Resvir-17 HA protein upon treatment with trypsin in the presence of 1% Zwittergent (left, A), or 1% SDS (right, B) in a time range from 15 minutes to 2 hours. HA0, and its subunits HA1 and HA2 are indicated by arrows.

In a subsequent experiment, the effect of column temperature on RP-HPLC of influenza A/Resvir-17 was again investigated, and at each test temperature samples were analyzed in triplicate. In addition, influenza A/New Caledonia (H1N1) was taken along (single injection at each temperature). As illustrated in FIG. 12B, the recovery of HA1 from influenza A/Resvir-17 (H3N2) was significantly enhanced when the column temperature was increased: between about 60° C. and 70° C. the HA1 peak area was the largest. No temperatures higher than 70° C. were explored (according to the manufacturer the maximum allowed temperature for this column is 80° C.). With regard to influenza A/New Caledonia (H1N1) a similar tendency was seen, although less pronounced as for influenza A/Resvir-17. At about 50, 60 and 70° C. more or less of an equilibrium with the same HA1 recoveries was acquired for A/New Caledonia. Consequently, the data described in this section point out that utilizing this particular column a column temperature between about 60° C. and 70° C. was optimal for RP-HPLC quantification of HA.

Example 6

Figure 16:
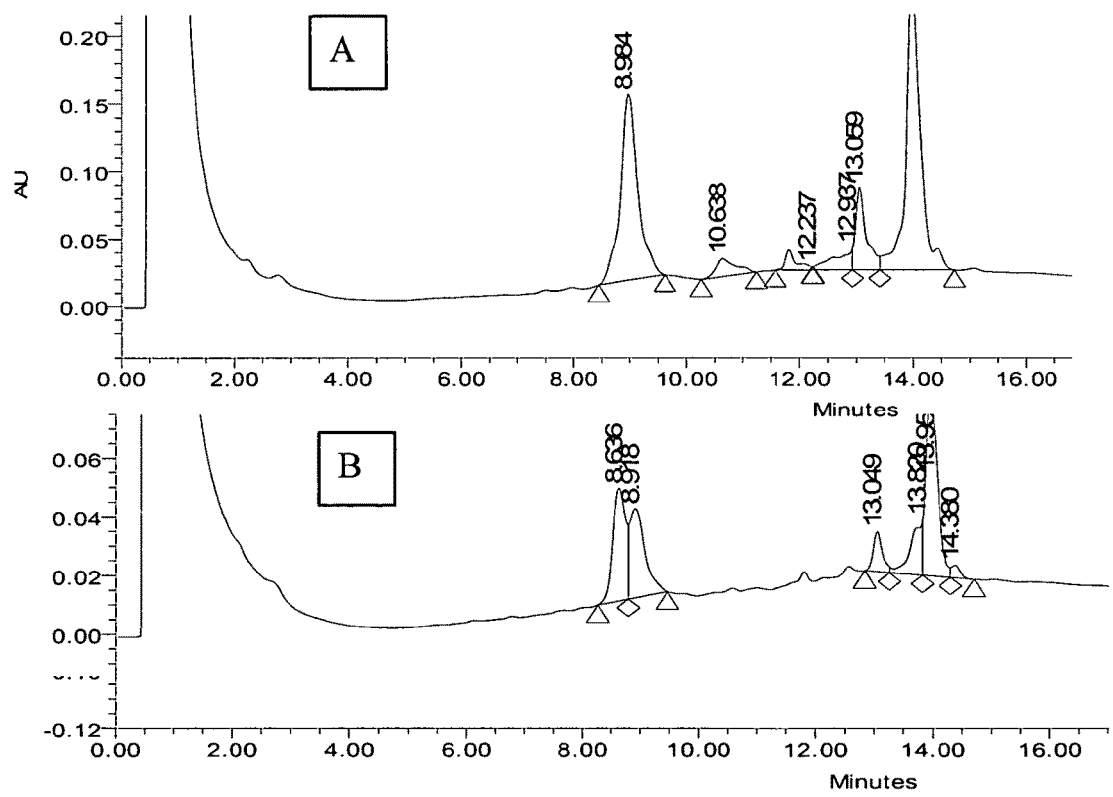
FIG. 16. RP-HPLC of non-trypsinized, reduced/alkylated, BPL-inactivated PER.C6® (immortalized, human embryonic retinoblast cell)-based influenza A/Resvir-17. (A) Immediate injection after reduction/alkylation (approximately 13.6 µg HA). (B) Injection after 17 hours storage at 4° C. (approximately 5.8 µg HA).

Determination of Hemagglutinin in Influenza Preparation of A/Equine/Prague/56 (H7N7) Using Reversed Phase HPLC It was further investigated whether the RP-HPLC assay was also applicable for hemagglutinin from influenza A subtype H7N7. Hence, the selectivity of the assay with formaldehyde-inactivated subtype A/Equine/Prague/56 (H7N7) was determined. Sample preparation and further procedures were generally as described in example 1 (1% SDS as detergent, reduction with 65 mM DTT, 65° C., 30 minutes, alkylation with IAA 116 mM, 37° C., 45 minutes in the dark). In FIG. 13, a Reversed Phase-HPLC chromatogram of the reduced and alkylated H7N7 antigen is shown. SDS-PAGE and subsequent silver staining (FIG. 14) of the proteins demonstrated that, based on the size of the protein as compared to the size marker, fraction 2 of FIG. 13, a relatively irregularly shaped peak, contained predominantly HA1 (FIG. 14, silver staining, Lanes depicted as “2”). Fraction 4 contained HA2 and the non-cleaved HA0 forms.

Taken together, as mentioned under example 2, these data demonstrate that the assay selectivity for quantification of HA1 is excellent, and in addition, that the RP-HPLC assay is not specific for a particular influenza A subtype, but that it can be applied broadly for different types of influenza viruses.

Example 7

Full Cleavage of HA0 in its Subunits HA1 and HA2

As noticed above, HA in both formaldehyde-inactivated egg-based and beta-propiolactone-inactivated PER.C6® (immortalized, human embryonic retinoblast cell)-derived influenza A/Resvir-17 (H3N2) did not turn out to be fully cleavable upon reduction (59 mM DTT, 30 minutes at 65° C.). This is a highly undesired situation, as the most accurate HA quantification by RP-HPLC requires a full cleavage of HA into HA1 and HA2. It was explored whether this could be accomplished by applying more severe reduction conditions. However, the ratio between non-cleaved HA0 and HA1 was not affected by reduction for longer times and/or at higher temperatures (data not shown). This indicated that most likely part of the HA in both preparations had not been cleaved enzymatically, and could therefore never be split upon reduction.

Then, it was investigated whether the cleavage of the residual un-cleaved HA was possible by additional trypsin treatment of both vaccines dissociated in 1% SDS or 1% Zwittergent. Under these conditions, HA is in its trimeric format, which is susceptible to the trypsin-induced specific cleavage into its subunits, but resistant to further proteolytic breakdown. For this, agarose beads conjugated with trypsin were utilized, which enables one to remove the beads conveniently by centrifugation after digestion, thereby also avoiding possible proteolytic degradation of trypsin-sensitive HA1 during the further sample preparation (e.g., the reduction step). Buffer solution was 134 mM Tris-HCL, pH 8.0 and reduction was performed with DTT at 100° C. for 10 minutes. Alkylation was performed by IAA treatment as in the previous examples. During trypsin treatment (15, 35, 60 and 120 minutes), samples were rotated in an oven at 37° C. to prevent the trypsin beads from precipitating in the sample tubes.

Pre-treatment of BPL-inactivated PER.C6® (immortalized, human embryonic retinoblast cell)-based Resvir-17 in 1% ZWITTERGENT® resulted in the disappearance of the residual amount of un-cleaved HA0, while further breakdown of HA1 and/or HA2 was not detected (left panel, FIG. 15). In contrast, trypsinization in the presence of 1% SDS did not lead to cleavage of the residual HA0 (right panel, FIG. 15), most likely because the trypsin activity was abolished by this concentration of denaturing SDS. Thus, when trypsin is used to fully cleave the HA0 protein, it is preferred not to use SDS, but rather to use a detergent such as ZWITTERGENT®. When the trypsinized sample in 1% ZWITTERGENT® was analysed by RP-HPLC and compared with Resvir-17 HA that was not treated with trypsin, an increase of up to 10% in HA1 peak area could be detected upon trypsin treatment prior to reduction and RP-HPLC analysis (Table 6). These data demonstrate that trypsin pre-treatment (30 minutes at 37° C.) is a highly preferred sample preparation step in the RP-HPLC method for HA quantification of influenza vaccines.

In contrast, the situation for formaldehyde-inactivated egg-based A/Resvir-17 was quite different: in the presence of either SDS or ZWITTERGENT® cleavage of HA0 by additional trypsin pre-treatment did not turn out to be possible (data not shown). This was most likely due to the formaldehyde-inactivation treatment (different from the beta-propiolactone treatment discussed above). Formaldehyde is known to cause irreversible cross-linking of proteins, which are in a complex, like the disulfide-linked HA1 and HA2. Consequently, it is preferred to use trypsin to ensure a full cleavage of HA0, but if trypsin is used it should be used in a detergent such as ZWITTERGENT®, rather than SDS, while trypsin should preferably be used on samples that were previously inactivated through an inactivating agent such as BPL, rather than cross-linking inactivating agents such as formaldehyde.

Example 8

Sample Stability: Effect of Reducing and Alkylation Conditions on RP-HPLC of HA of A/Resvir-17 (H3N2)

Initially, influenza samples were reduced and alkylated under non-buffered conditions. When injected immediately after the non-buffered reduction and alkylation reactions (1% ZWITTERGENT®; reduction 59 mM DTT, 65° C. 30 min.; alkylation 106 mM IAA, 37° C. 45 minutes in the dark), RP-HPLC of PER.C6® (immortalized, human embryonic retinoblast cell)-based A/Resvir-17 HA resulted in a sharp HA1 peak, eluting at approximately 8.9 minutes in the chromatogram (FIG. 16, panel A). However, it was noted that this sample was unstable: overnight storage of this batch (approximately 17 hours) at 4° C. gave rise to a novel peak at 8.6 minutes, which was accompanied by a decrease of the original HA1 peak eluting at 8.9 minutes (FIG. 16, panel B). This suggested that part of the HA1 became slightly more hydrophilic in time. Similar observations were made for egg-based Resvir-17. First, it was thought that this phenomenon was related to the non-buffered status of the samples. However, this did not appear to be the only explanation, because in another PER.C6® (immortalized, human embryonic retinoblast cell)-based influenza A/Resvir-17 batch (1% ZWITTERGENT®, reduction with 57 mM DTT 10 minutes at 100° C., buffered at pH 8.0, alkylation with 102 mM IAA 45 minutes at 37° C. in the dark), stored at 21° C. instead of 4° C., comparable changes in the HA1 peak shape occurred (FIG. 17A), although to a lesser extent as shown in FIG. 16B.

Figure 17:
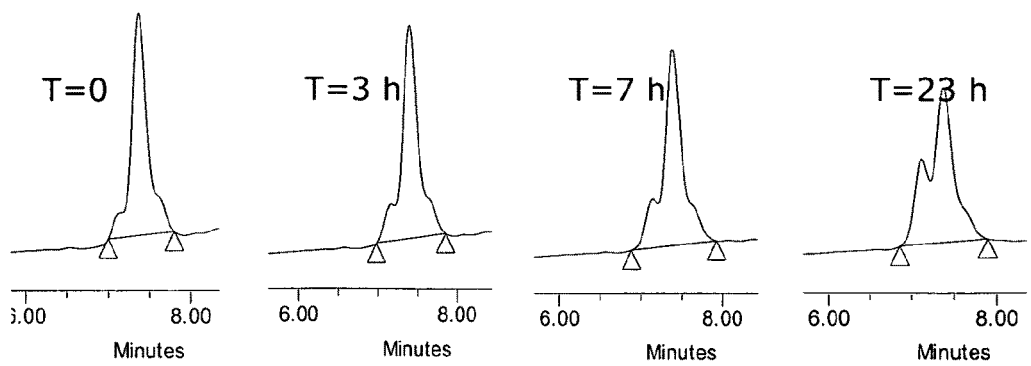
FIG. 17. HA1 peak shape monitoring of non-trypsinized influenza A/Resvir-17 after reduction and alkylation (A), or after reduction only (B).
Figure 17:
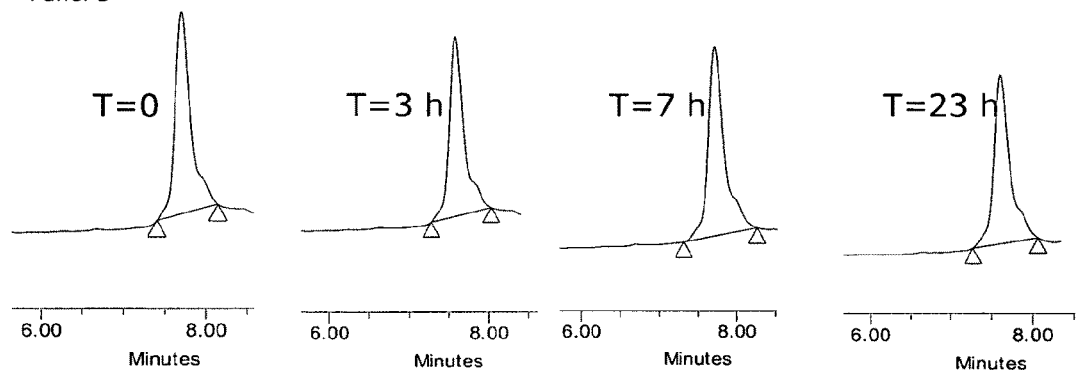

On the other hand, the observed HA1 peak deformation in time might also be caused by the presence of residual amounts of IAA, as it is generally known that IAA may give rise to relatively strong adverse effects on the integrity of proteins. Then, the effect of omission of the alkylation step after reduction was studied. This however, did not have a significant effect on HA1 recovery, but, interestingly, regarding the HA1 peak shape, samples proved to be far more stable in time (FIG. 17B). Consequently, the data as depicted in FIG. 17 suggest that HA1 was relatively stable for 23 hours at 21° C. under strictly reducing conditions (DTT), but not when most (if not all) DTT was neutralized by IAA.

Figure 18:
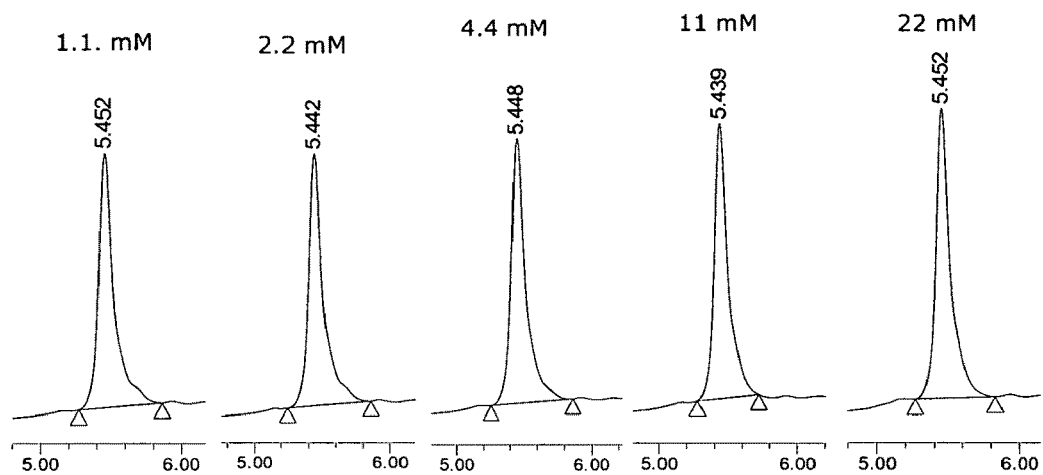
FIG. 18. HA1 peak shape monitoring of non-trypsinized influenza A/Resvir-17 after reduction by DTT with different concentrations and subsequent storage at 4° C. for 0 hours (A) or for 18 hours (B).
Figure 18:
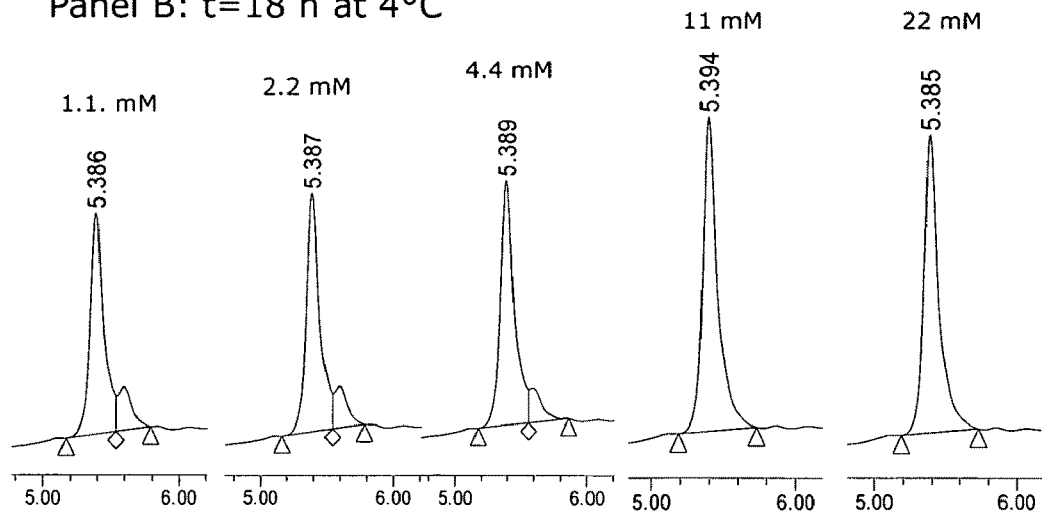

To distinguish whether the apparent HA1 instability was due to the absence of reducing circumstances or to possible disadvantageous side effects of the residual amount of IAA chemically modifying the protein, the HA1 stability was also monitored after reduction (without subsequent alkylation) at various DTT concentrations before and after storage for 18 hours at 4° C. As can be seen in FIG. 18, at all tested DTT concentrations (1.1, 2.2, 4.4, 11 and 22 mM), the previously observed additional peak that eluted just before the original HA1 peak (see FIGS. 16B and 17A) was not observed anymore, when stored for at least 18 hours (panel B), indicating that the HA1 peak transformation must have been caused by the IAA-related chemical modifications of the protein.

Unexpectedly, a different (putative) HA1-peak instability was observed: after 18 hours at 4° C. and at low DTT-concentrations (1-4 mM) a small, but significant peak was discernible in the tailing part of the original HA1 peak (FIG. 18B). At higher DTT concentrations (11 and 22 mM), this little peak did not evolve. So, these higher concentrations of DTT are preferred. Overall, it is preferred to use concentrations of DTT higher than about 4.4 mM, more preferably at least about 11 mM and most preferably about 22-25 mM.

Figure 19:
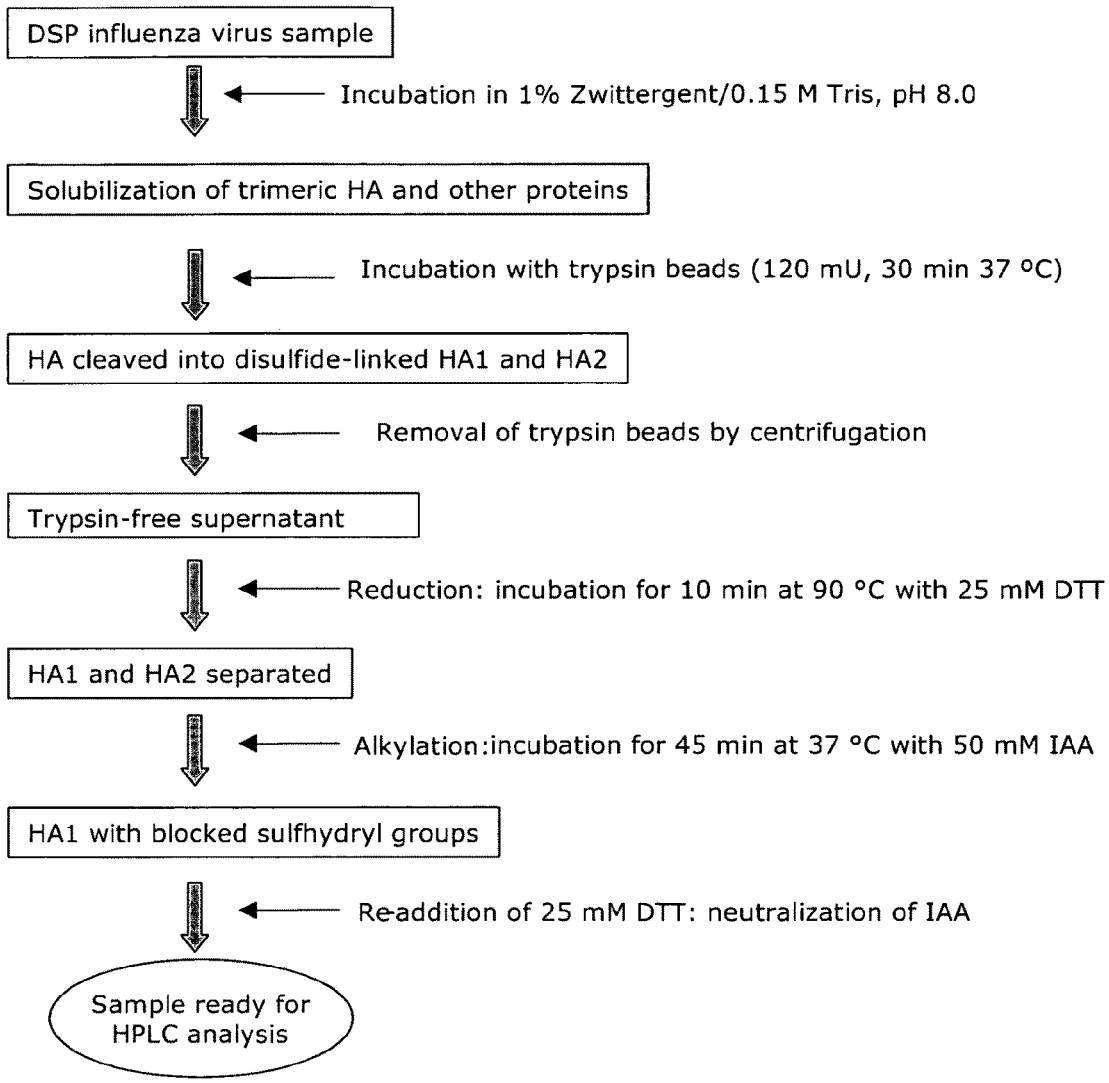
FIG. 19. Schematic flow-sheet of a preferred embodiment of the method of the invention indicating the preferred steps of trypsin incubation and the re-addition of the reducing agent after the alkylation step at a concentration of 25 mM, thereby reducing the undesired effects of the alkylating agent.

The stability of the HA1 peak area was monitored in triplicate for both a reduced/alkylated/DTT treated sample and an only reduced PER.C6® (immortalized, human embryonic retinoblast cell)-based influenza A/Resvir-17 sample before and after storage for 20 hours at 4° C. Notably, reduction was carried out at a DTT concentration of 25 mM, and after the alkylation reaction (as for half of the samples) DTT was re-added to a final concentration of 25 mM, to prevent any HA1 peak deformation. It turned out that, unlike the experiment of FIG. 18, the HA1 peak area was barely, if at all, affected by storage for 20 hours at 4° C. (Table 7). Importantly, it was noticed that upon reduction/alkylation and re-addition of DTT to the samples the HA1 recovery seemed to be at least 6 to 10% higher than after reduction alone. A possible explanation is that alkylated HA1 exhibits less (non-specific) absorption to the column than its non-alkylated counterpart. An alternative explanation might be that the molar extinction coefficient of HA1 was enhanced by the alkylation, leading to relatively higher signals at 215 nm. Whatever the reason, based on the data of Table 7, it is highly preferred to include the step of adding the reducing agent after alkylation in the sample preparation procedure. Similar results were obtained with the influenza A/New Caledonia (H1N1) strain derived from eggs. This embodiment of the method of the invention is depicted schematically in the flow diagram of FIG. 19.

Example 9

Effect of Trypsin Concentration on Recovery of HA1

Figure 20:
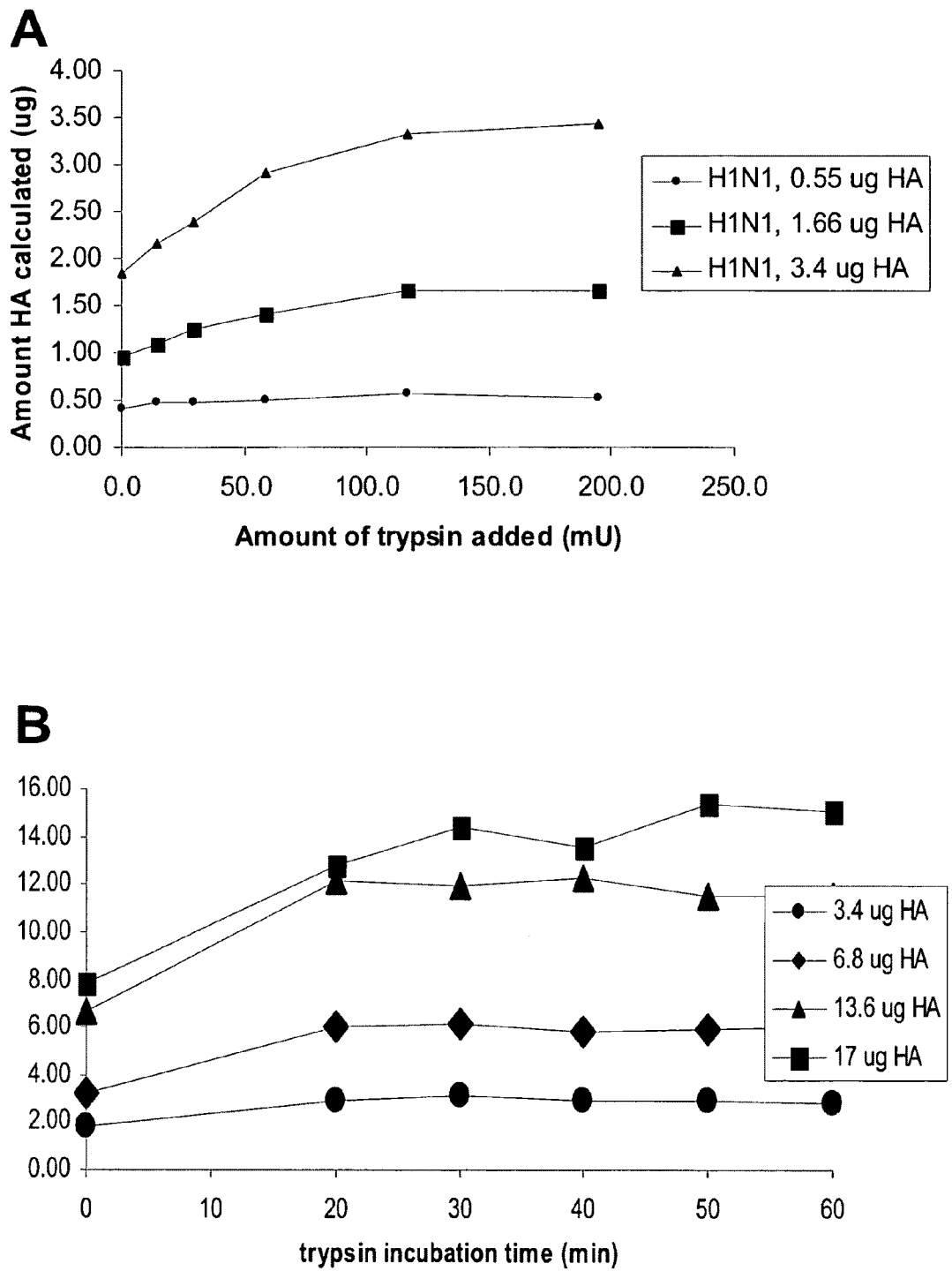
FIG. 20. (A) Effect of increasing amount of trypsin (mU) added to influenza preparations of A/New Caledonia, containing small amounts of HA, and (B) increasing times of trypsin treatment (using 120 mU).

Above, it has been indicated that trypsin treatment ensures a full cleavage of HA into its subunits HA1 and HA2. It should be noted that if the cleavage, due to for instance cellular proteases may be complete and that an extra trypsin treatment may be omitted. Nevertheless, to ensure that all HA0 is cleaved, it is preferred to add the additional trypsin step. An experiment was designed to explore the effect of increasing concentrations of trypsin (preferably present on beads) on the ultimate recovery of HA1 from three samples of PER.C6® (immortalized, human embryonic retinoblast cell)-based influenza A/New Caledonia, which differed in the amount of virus and, hence, in HA content. It turned out that for each of the three samples addition of 120 mU trypsin beads, and subsequent incubation for 30 minutes at 37° C. resulted in optimal HA1 recoveries (FIG. 20A). It was also investigated whether these conditions were suitable for batches, containing higher amounts of influenza virus, having HA titers of approx. 3.4, 6.8, 13.6, and 17 µg/ml. As illustrated in FIG. 20B, this was indeed the case for the influenza samples containing up to 13.6 µg HA/ml: the maximal recovery of HA1 from these samples was attained after 30 minutes incubation at 37° C. with 120 mU trypsin beads and longer incubation times did not lead to higher HA1 peak areas. As for preps with higher concentrations of influenza virus most likely longer incubation times may be required.

Example 10

Comparison RP-HPLC System Versus SRID

As disclosed herein, it was demonstrated that the assay selectivity, linearity and precision of the method according to the invention were good. To explore whether the RP-HPLC assay according to the invention would provide for a proper alternative for the cumbersome and slow SRID assay, results were compared between the two assays. In Table 8, a first comparison was made between both assays for a number of A/Resvir-17 samples. It must be noted that trypsin pretreatment and alkylation were not included as standard steps. Six different samples were compared, whereas the concentration of the samples A, C and D were determined in triplicate by HPLC (e.g., A1, A2, A3). The Table shows that the HA titers obtained by RP-HPLC closely resembled those acquired by SRID.

Interestingly, the data also demonstrated that formaldehyde treatment of A/Resvir-17 resulted in a greatly reduced HA1 peak as compared to the same, but BPL-inactivated batch (Table 8; compare samples E and F), supporting earlier conclusions that HA quantification in formaldehyde-inactivated influenza batches is far from accurate.

Subsequently, these comparative studies between RP-HPLC and SRID were repeated in more detail for a series of A/New Caledonia samples. As shown in Table 9, the HPLC data agreed well with the SRID-based titres. Consequently, it was thus established that the RP-HPLC assay is accurate, and represents a good alternative for the SRID assay to quantify the HA concentration in influenza virus containing batches. This is certainly the case when taking into account that the HPLC assay precision is better than the precision attained by SRID (Table 9, see RSD values for sample D).

Example 11

HA Quantification in Crude Samples

Figure 21:
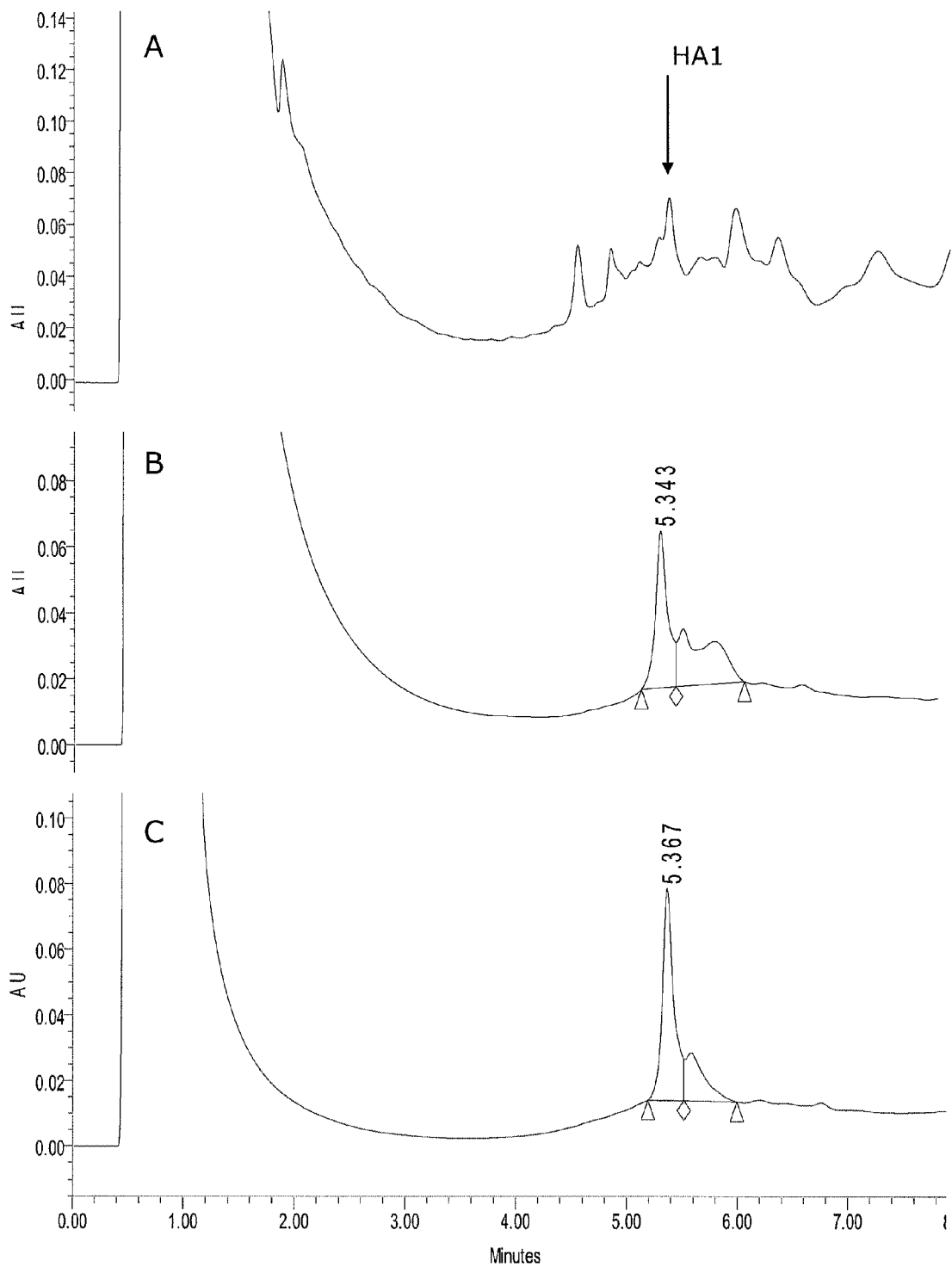
FIG. 21. RP-HPLC of: (A) a culture supernatant of PER.C6® cells (immortalized, human embryonic retinoblast cells) grown in BMIV medium and infected with influenza A/Resvir-17; (B) a trypsin-treated (192 mU) culture supernatant as in (A); and (C) a trypsin-treated (192 mU) and centrifuged pellet of culture supernatant as in (A).
Figure 22:
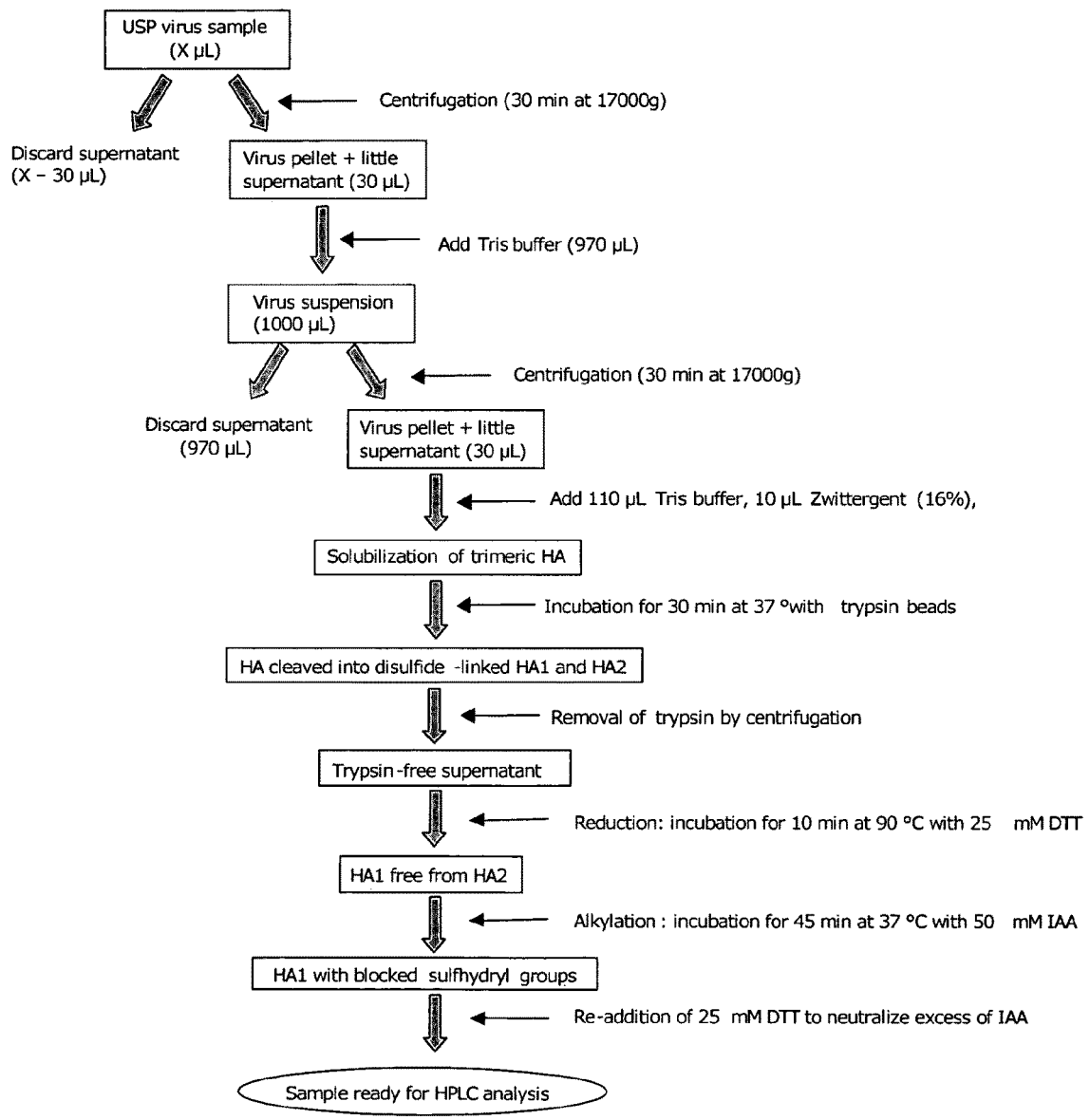
FIG. 22. Flow diagram of the preferred steps involved in the preparation of crude culture supernatants containing influenza virus, for quantification of HA by RP-HPLC.

From a process development point of view, another important application of the assay would be measuring the HA concentration in crude culture supernatants of cells infected with influenza virus. To explore the feasibility of this potential application we studied the assay selectivity with regard to the sample matrix, i.e., conditioned growth medium of PER.C6® cells (immortalized, human embryonic retinoblast cells. When analyzing a sample of a crude culture supernatant of PER.C6® cells (immortalized, human embryonic retinoblast cells) grown in AEM medium and infected with influenza A/Resvir-17 without any sample treatment other than reduction alone, a rather complex chromatogram was recorded (FIG. 21A). Although a peak was discernible having the same retention time as HA1 (FIG. 21A, indicated by an arrow), it became immediately clear that quantification of HA1 by measuring the HA1 peak area was impossible due to the large amount of interfering material surrounding the putative HA 1 peak. It was reasoned that an additional trypsin treatment might solve the observed problem of lack of assay selectivity for crude samples by digesting the interfering proteins in the sample. This indeed turned out to be the case, as the RP-chromatogram of a comparable culture supernatant pre-treated with trypsin (coupled to agarose beads) exhibited a HA1 peak almost free from other material and thus relatively easy to integrate (FIG. 21B). However, as it could not be excluded that part of the HA1 might have been broken down during (further) preparation of this sample due to the presence of soluble trypsin, which is already present in cell cultures when the influenza viral infection has to be stimulated (general procedure), it was also investigated whether the HA1 recovery could be augmented by first centrifuging the virus, and then treating the virus pellet with the trypsin beads (after removal of the supernatant containing the soluble trypsin). It appeared that this approach indeed resulted in a significantly (about 30%) enhanced HA1 peak area (FIG. 21C). Thus, for routine crude sample analysis for quantification of HA it is preferred to include at least one centrifugation step in the sample preparation to remove the harmful soluble trypsin and proteins, which interfere with the integration of the HA1 peak in the chromatogram. Another advantage is that the virus is concentrated by this strategy. Centrifugation is typically performed for 30 minutes at 4° C. with centrifugal force values of 4500 g or higher, preferably higher than 6000, more preferably higher than 9000, even more preferably higher than 12,000 g, whereas the it is most preferred to use at least 17,000 g, because the HA recovery values were up to 100% when 12,000 g to 17,000 g was used. One preferred embodiment of the method according to the invention in which HA1 is quantified in crude (supernatant) samples of cells infected with influenza viruses is shown in FIG. 22.

TABLE 1

Gradient profile of the RP-HPLC influenza quantification method. Solvent A is 0.1% trifluoracetic acid (TFA) in 5% acetonitrile, solvent B is 0.098% TFA in 100% acetonitrile.

| Time (minutes) | Percentage solvent A | Percentage solvent B |
|---|---|---|
| 0 | 80 | 20 |
| 11 | 65 | 35 |
| 16 | 62.5 | 37.5 |
| 16.5 | 40 | 60 |
| 17 | 0 | 100 |
| 21 | 0 | 100 |
| 21.5 | 80 | 20 |
| 26 | 80 | 20 |

TABLE 2

RP-HPLC assay precision (or repeatability) data of six injections of an egg-derived, reduced and alkylated sample of influenza A/New Caledonia H1N1. Amount HA per injection was 0.65 μg.

| Sample | HA1 peak area |
|---|---|
| 1 | 296602 |
| 2 | 276102 |
| 3 | 274735 |
| 4 | 264570 |
| 5 | 279309 |
| 6 | 312359 |
| Average | 283946 |
| STDEV | 17383 |
| % CV | 6.1 |

TABLE 3

RP-HPLC assay precision data of four independently reduced and alkylated samples of egg-derived influenza A/New Caledonia H1N1. Amount HA per injection was 3.0 μg.

| Sample | HA1 peak area |
|---|---|
| 1 | 2270955 |
| 2 | 2330900 |
| 3 | 2249605 |
| 4 | 2365733 |
| Average | 2304298 |
| STDEV | 53495 |
| % CV | 2.3 |

TABLE 4

Gradient profile of the RP-HPLC influenza quantification method. Solvent A is 0.1% trifluoracetic acid (TFA) in 5% acetonitrile, solvent B is 0.098% TFA in 100% acetonitrile.

| Time (minutes) | Percentage solvent A | Percentage solvent B |
|---|---|---|
| 0 | 80 | 20 |
| 11 | 65 | 35 |
| 21 | 60 | 40 |
| 25 | 40 | 60 |
| 28 | 40 | 60 |
| 28.5 | 0 | 100 |
| 34 | 0 | 100 |
| 34.5 | 80 | 20 |
| 40 | 80 | 20 |

TABLE 5

Effect of column temperature on RP-HPLC of egg-derived, reduced and alkylated Resvir-17 antigen (H3N2).

| Temperature | | Peak Area (215 nm) | | |
|---|---|---|---|---|
| | HA1 | Peak 2 | Peak 3 | Peak 4 |
| 25 | 1084581 (8.51) | 79310 (14.57) | ? | 236605 (27.41) |
| 40 | 1092810 (8.32) | 112307 (14.19) | ? | 264513 (27.51) |
| 50 | 1150764 (8.08) | 165212 (13.75) | 18343 (22.73) | 302645 (27.48) |
| 60 | 1231606 (7.74) | 220181 (13.15) | 36399 (21.38) | 337627 (27.37) |
| 70 | 1200473 (7.35) | 239249 (12.44) | 63262 (19.60) | 354590 (27.21) |

TABLE 6

Effect of pre-treatment of influenza A/Resvir-17 sample with trypsin on the peak area of HA1 in RP-chromatograms

|  | HA1 peak area | |
|---|---|---|
| Sample no. | Trypsin-treated | Un-treated |
| 1 | 309195 | 284591 |
| 2 | 307957 | 290161 |
| 3 | 307849 | 221986 |
| Average | 308334 | 265579 |
| % CV | 0.24% | 14.3% |

TABLE 7

Effect of reduction/alkylation/DTT treatment versus reduction only on the recovery of HA1 derived from a non-trypsinized PER.C6 ® (immortalized, human embryonic retinoblast cell)-based influenza A/Resvir-17 batch (H3N2) measured by RP-HPLC. Amounts injected: approximately 2.9 µg HA.

| | HA1 peak area (t = 0 h) | | | HA1 peak area (t = 20 h) | |
|---|---|---|---|---|---|
| Sample | red | red/alk/DTT | Sample | red | red/alk/DTT |
| 1 | 673460 | 745625 | 1 | 663174 | 715848 |
| 2 | 667988 | 738530 | 2 | 669209 | 698951 |
| 3 | 698279 | 762926 | 3 | 698670 | 742749 |
| Average | 679909 | 749027 | Average | 677018 | 719183 |
| STDEV | 16142 | 12549 | STDEV | 18993 | 22089 |
| RSD | 2.4 | 1.7 | RSD | 2.8 | 3.1 |
| | 100% | 100% | | 99.6 | 96.0% |

TABLE 8

Comparison of the HA titers of seven A/Resvir-17 samples determined by RP-HPLC and SRID. An A/Resvir-17 batch with a HA concentration of 1161 µg HA/ml was taken as reference (for calibration in HPLC).

| Sample | HA1 peak area | Amount HA inj. (ug) | HA conc. (ug/ml) | SRID-titer (ug/ml) |
|---|---|---|---|---|
| A1 | 1285946 | 5.5 | 314.2 | 271.7 |
| A2 | 1279305 | 5.5 | 312.7 | |
| A3 | 1218873 | 5.3 | 298.9 | |
| B | 1017237 | 4.5 | 56.2 | 44.6 |
| C1 | 1572872 | 6.7 | 759.1 | 822.2 |
| C2 | 1516648 | 6.5 | 733.5 | |
| C3 | 1667708 | 7.1 | 802.3 | |
| D1 | 1058261 | 4.6 | 262.3 | 260.6 |
| D2 | 1065175 | 4.7 | 263.9 | |
| D3 | 1060703 | 4.6 | 262.9 | |
| E Formaldehyde inactive | 29183 | 0.5 | 55.8 | out of range |
| F BPL inactive | 531782 | 2.5 | 284.8 | out of range |

TABLE 9

Comparison of the HA titers of 5 influenza A/New Caledonia samples (A-D) determined by RP-HPLC and SRID. Different fractions were taken. An A/New Caledonia batch with a HA concentration of 90 µg HA/ml was taken as reference (for calibration in HPLC).

| | HA titer (µg/mL) | |
|---|---|---|
| A/New Caledonia | SRID | HPLC |
| A #1 crude | 18.4 | 17.9 |
| A #2 sup | 8.7 | 11.1 |
| A #3 clarified | <LOQ | 10.2 |

TABLE 9-continued

Comparison of the HA titers of 5 influenza A/New Caledonia samples (A-D) determined by RP-HPLC and SRID. Different fractions were taken. An A/New Caledonia batch with a HA concentration of 90 µg HA/ml was taken as reference (for calibration in HPLC).

| | HA titer (µg/mL) | |
|---|---|---|
| A/New Caledonia | SRID | HPLC |
| A #4 conc | 64.6 | 90.0 |
| A #5 permeate | <LOQ | 0.5 |
| B fraction 1 | 26.9 | 19.6 |
| B fraction 2 | 69.6 | 73.6 |
| B fraction 3 | 11.0 | 11.5 |
| B sucrose fraction | <LOQ | 3.1 |
| C virusband | 93.2 | 86.3 |
| C sucrose fraction | <LOQ | 4.3 |
| D BPL-inact. | 82.6 | 79.6 |
| D1 conc (2) | 540.6 | 591.6 |
| D2 conc (2) | 614.6 | |
| D PBS-fraction | <LOQ | 1.5 |
| D final product | 488.5 | 552.8 |
| | 502.0 | 559.3 |
| | 407.2 | 563.7 |
| | 556.9 | |
| final prod. (average) | 488.7 | 558.6 |
| STDEV | 61.8 | 5.5 |
| RSD | 12.7 | 1.0 |

REFERENCES

Bizhanov, Kastrikina, Lonskaya, and Popov (1988). Influence of detergents on measurement of influenza haemagglutinin content in inactivated influenza vaccine by single radial immunodiffusion. *Acta. Virol.* 32:252-260.

Johannsen, Moser, Hinz, Friesen, and Gruschkau (1985). Quantification of hemagglutinin of influenza Tween-ether split vaccines by immunodiffusion. *Vaccine* 3, Suppl 1985: 235-240.

Kemp M. C., Holloway, Bennett and Compans (1980). Separation of Influenza hemagglutinin tryptic glycopeptides by ion-pair Reverse-Phase High-Performance Liquid Chromatography (HPLC). *J. Biochem. and Biophys. Methods* 3:61-63.

Lamb and Krug (2001). Orthomyxoviridae: the viruses and their replication. In: *Fields Virology* Vol. 1 (4$^{th}$ edition), pp. J487-1531. Eds. Knipe, Howley, Griffin, Martin, Lamb, and Roizman, Lippincott, Williams & Wilkins, Philadelphia.

Pereira (1973). Final discussion on standardization of influenza vaccines. *Symp. Ser. Immunobiol. Stand.* 20:378.

Phelan and Cohen (1983). Gradient optimization principles in reversed-phase high performance liquid chromatography and the separation of influenza virus components. *J. Chromatography* 266:55-66.

Van der Zee R., Welling-Wester and Welling (1983). Purification of detergent-extracted Sendai virus proteins by Reversed-Phase High-Performance Liquid Chromatography. *J. Chromatography* 266:577-584.

Villkommen, Platen, and Staber (1983). The influence of pH and ionic strength on the single-radial-immunodiffusion test quantitative assay of influenza virus haemagglutinin. *Acta. Virol.* 27:407-411.

Wood, Schild, Newman, and Seagroatt (1977). An improved single-radial-immunodiffusion technique for the assay of influenza haemagglutinin antigen: application for potency determinations of inactivated whole virus and subunit vaccines. *J. Biol. Stand.* 5:237-247.

Wright and Webster (2001). Orthomyxoviruses. In: *Fields Virology* Vol. 1 (4th edition), pp. 1533-1578. Eds. Knipe, Howley, Griffin, Martin, Lamb, and Roizman, Lippincott, Williams & Wilkins, Philadelphia.

What is claimed is:

1. A method for quantifying a hemagglutinin ("HA") titer of an influenza antigen preparation comprising HA, the method comprising
   applying a reduced and derivatized antigen preparation comprising solubilized influenza HA that is cleaved into subunits HA1 and HA2 and a detergent in a pH controlled solution to a Reversed-Phase High-Performance Liquid Chromatography (RP-HPLC) column in an RP-HPLC system;
   eluting HA antigens from the RP-HPLC column with an ion-pairing agent in an organic mobile phase, and further wherein the HA antigens are derivatized with an alkylating agent; and
   measuring a peak area of the HA1 subunit of influenza HA in a chromatogram resulting from the elution to determine the HA titer of the influenza HA antigen preparation based on calibration of the RP-HPLC system with a reference concentration of influenza HA.

2. The method according to claim 1, wherein the influenza HA is cleaved into subunits HA1 and HA2 by trypsin.

3. The method according to claim 2, wherein the trypsin is present on beads.

4. The method according to claim 1, wherein a reducing agent is added to the derivatized antigen preparation after derivatization with an alkylating agent.

5. The method according to claim 1, wherein eluting is performed with a column comprising polymer-based material.

6. The method according to claim 1, wherein the method is a high-throughput method.

7. A method for quantifying the hemagglutinin ("HA") titer of an influenza A or influenza B antigen preparation comprising HA, the method comprising
   separating HA antigens from an influenza A or influenza B virus by a method comprising:
      obtaining a preparation comprising HA antigens from influenza A or influenza B virus;
      solubilizing the antigens by a detergent in a pH controlled solution;
      cleaving the HA antigens into HA1 and HA2 with a protease;
      reducing the HA1 and HA2 antigens with a reducing agent;
      derivatizing the HA1 and HA2 antigens with an alkylating agent;
      applying the antigen preparation on a Reversed-Phase High-Performance Liquid Chromatography ("RP-HPLC") column;
   eluting HA1 and HA2 antigens from the RP-HPLC column with an ion pairing agent in an organic mobile phase, thereby separating the HA1 antigen from HA2 antigen; and
   measuring the peak area of eluted HA1 antigen in a chromatogram resulting from the elution step to quantify the HA titer of the antigen preparation.

8. The method according to claim 7, wherein the protease is trypsin.

9. The method according to claim 8, wherein the trypsin is present on beads.

10. The method according to claim 7, wherein the alkylating agent is iodoacetamide.

11. The method according to claim 7, wherein the detergent is SDS or a zwitterionic detergent.

12. The method according to claim 7, wherein the reducing agent is dithiothreitol (DTT).

13. The method according to claim 7, wherein eluting is performed with a column comprising polymer-based material.

14. The method according to claim 7, wherein the method is a high-throughput method.

15. A method for quantifying the hemagglutinin (HA) titer of an influenza antigen preparation comprising HA, the method comprising:
   separating HA antigens from an influenza virus by a method comprising:
      obtaining a preparation comprising HA antigens from influenza virus;
      solubilizing the antigens by a detergent in a pH controlled solution;
      cleaving the HA antigens into HA1 and HA2 with a protease;
      reducing the HA1 and HA2 antigens with a reducing agent;
      derivatizing the HA1 and HA2 antigens with an alkylating agent;
      adding reducing agent after alkylation;
      applying the antigen preparation on a Reversed-Phase High-Performance Liquid Chromatography (RP-HPLC) column;
   eluting HA1 and HA2 antigens from the RP-HPLC column with an ion pairing agent in an organic mobile phase, thereby separating HA1 from HA2; and
   measuring the peak area of eluted HA1 antigen in a chromatogram resulting from the elution to quantify the HA titer of the antigen preparation.

16. The method according to claim 15, wherein the protease is trypsin.

17. The method according to claim 16, wherein the trypsin is present on beads.

18. The method according to claim 15, wherein eluting is performed with a column comprising polymer-based material.

19. The method according to claim 15, wherein the alkylating agent is iodoacetamide.

20. The method according to claim 15, wherein the method is a high-throughput method.

* * * * *